United States Patent
Nagai et al.

(10) Patent No.: US 8,082,113 B2
(45) Date of Patent: Dec. 20, 2011

(54) SAMPLE ANALYSIS SYSTEM AND REAGENT PREPARATION DEVICE

(75) Inventors: Takaaki Nagai, Kobe (JP); Masaharu Shibata, Kobe (JP); Kunio Ueno, Kakogawa (JP); Noriyuki Nakanishi, Kakogawa (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 12/715,755

(22) Filed: Mar. 2, 2010

(65) Prior Publication Data

US 2010/0161243 A1    Jun. 24, 2010

Related U.S. Application Data

(63) Continuation of application No. PCT/JP2008/065487, filed on Aug. 29, 2008.

(30) Foreign Application Priority Data

Sep. 3, 2007    (JP) ................................ 2007-228025

(51) Int. Cl.
  *G06F 19/00*  (2011.01)
  *C12M 1/36*  (2006.01)
  *G01N 27/417*  (2006.01)
  *G01N 1/00*  (2006.01)

(52) U.S. Cl. .................. 702/25; 435/286.5; 422/82.05; 436/179; 73/863

(58) Field of Classification Search .................. 702/25; 435/287.1, 286.5; 422/63, 82.05; 436/179; 73/863

See application file for complete search history.

(56) References Cited

U.S. PATENT DOCUMENTS

| 5,800,056 A | 9/1998 | Suzuki et al. |
| 2009/0035873 A1 * | 2/2009 | Shibata ........................ 436/179 |

FOREIGN PATENT DOCUMENTS

| JP | 01-167660 A | 7/1989 |
| JP | 05-293448 A | 11/1993 |
| JP | 06-265555 A | 9/1994 |
| JP | 08-062852 A | 3/1996 |
| JP | 09-033538 A | 2/1997 |
| JP | 11-007324 A | 1/1999 |
| JP | 2000-266763 A | 9/2000 |
| JP | 2006-071649 A | 3/2006 |
| JP | 2007-205763 A | 8/2007 |

OTHER PUBLICATIONS

International Search Report for International Application No. PCT/JP2008/065487, dated Dec. 9, 2008, 2 pages.

* cited by examiner

*Primary Examiner* — Bryan Bui
(74) *Attorney, Agent, or Firm* — Brinks Hofer Gilson & Lione

(57) ABSTRACT

A sample analysis system includes a reagent preparation unit and a measurement unit. The reagent preparation unit has: a state detector which detects at least one of a state of the reagent preparation unit and a state of the reagent preparation; and a transmission unit which transmits the detected state information to a computer arranged outside the reagent preparation unit. The computer displays the received state information on a display.

22 Claims, 19 Drawing Sheets

SAMPLE ANALYSIS SYSTEM AND REAGENT PREPARATION DEVICE

RELATED APPLICATIONS

This application is a continuation of PCT/JP2008/065487 filed on Aug. 29, 2008, which claims priority to Japanese Application No. JP2007-228025 filed on Sep. 3, 2007. The entire contents of these applications are incorporated herein by reference.

BACKGROUND OF THE INVENTION

1. Field of the Invention

The present invention relates to a sample analysis system, a reagent preparation device and a sample treating device, and more particularly, it relates to a sample analysis system, a reagent preparation device and a sample treating device each preparing a reagent by diluting a high-concentration reagent with a dilution liquid.

2. Description of the Related Art

A reagent preparation device preparing a reagent by diluting a high-concentration reagent with a dilution liquid is known in general. Such a reagent preparation device is disclosed in Japanese Patent Laying-Open No. 9-33538, for example.

The aforementioned Japanese Patent Laying-Open No. 9-33538 discloses a reagent preparation device comprising a preparation tank for storing a high-concentration reagent and pure water (dilution liquid), a reagent constant amount tank supplying a prescribed amount of the high-concentration reagent to the preparation tank, a pure water constant amount tank quantifying and supplying pure water to the preparation tank, a diaphragm pump capable of replenishing pure water to the preparation tank little by little in response to the frequency of operations, a sensor (detection unit) detecting electrical conductance of the reagent diluted in the preparation tank, and a control unit controlling an operation of the diaphragm pump. In this reagent preparation device, the high-concentration reagent is not prepared at a desired concentration in one step, but the high-concentration reagent is first prepared at a relatively high concentration in the preparation tank. Then, in the reagent preparation device, a small amount of pure water is added into the preparation tank by the diaphragm pump while monitoring the electrical conductance of the reagent in the preparation tank by utilizing that the electrical conductance of the reagent and the concentration of the reagent are correlated. Thus, the reagent in the preparation tank approaches a desired concentration. In this reagent preparation device, the frequency of operations of the diaphragm pump in adding the small amount of pure water is calculated with a value of the electrical conductance of the reagent in the preparation tank varying with a single operation of the diaphragm pump (hereinafter referred to as a "value of a variable of electrical conductance").

However, the aforementioned value of the variable of the electrical conductance employed in the reagent preparation device of the aforementioned Japanese Patent Laying-Open No. 9-33538 is previously obtained by an experiment. Therefore, in a case where a high-concentration reagent is diluted with a dilution liquid different in property from the dilution liquid employed in the experiment, when the frequency of operations of the diaphragm pump is calculated with the aforementioned value of the variable of the electrical conductance, the high-concentration reagent may not be able to be diluted at the desired concentration.

SUMMARY OF THE INVENTION

The scope of the present invention is defined solely by the appended claims, and is not affected to any degree by the statements within this summary.

A sample analysis system according to a first aspect of the present invention comprises a reagent preparation unit for preparing a reagent employed in sample measurement by diluting a high-concentration reagent with a dilution liquid, and a measurement unit connected to the reagent preparation unit and for measuring a sample with the reagent prepared by the reagent preparation unit, wherein the reagent preparation unit comprises a state detector detecting at least one of a state of the reagent preparation unit and a state of reagent preparation by the reagent preparation unit, and a transmission unit for transmitting state information detected by the state detector to a computer arranged outside the reagent preparation unit, and the computer comprises a display, receives the state information transmitted by the transmission unit of the reagent preparation unit, and displays the received state information on the display.

A reagent preparation device according to a second aspect of the present invention is constituted to prepare a reagent employed in sample measurement by diluting a high-concentration reagent with a dilution liquid, and comprises a state detector for detecting at least one of a state of the reagent preparation device and a state of reagent preparation, and a transmission unit for transmitting state information detected by the state detector to a computer arranged outside the reagent preparation device, wherein the computer comprises a display, receives the state information transmitted by the transmission unit, and displays the received state information on the display.

A reagent preparation device according to a third aspect of the present invention is a reagent preparation device for preparing a reagent employed in sample processing device by diluting a high-concentration reagent with a dilution liquid, and comprises a storage unit storing the high-concentration reagent and the dilution liquid, first supplier for supplying the dilution liquid to the storage unit, a detector for detecting a value regarding a prescribed feature of the dilution liquid, second supplier for supplying the high-concentration reagent to the storage unit, a controller for controlling the first supply means so as to supply a prescribed amount of the dilution liquid to the storage unit, and controlling the second supply means so as to supply a prescribed amount of the high-concentration reagent to the storage unit, and decision means for deciding a target value of a value regarding the prescribed feature of a liquid obtained by mixing the high-concentration reagent and the dilution liquid in the storage unit, on the basis of a detection value detected by the detector.

DETAILED DESCRIPTION OF THE PREFERRED EMBODIMENTS

Embodiments of the present invention will be hereinafter described with reference to the drawings.

First Embodiment

A structure of a blood analysis device 1 according to a first embodiment of the present invention will be now described with reference to FIGS. 1 to 7. While the blood analysis device 1 is constituted as a multiple blood cell analysis device for performing a blood test, only measurement of white blood cells, reticulocytes and blood platelets in blood will be described in the following description.

Figure 1:
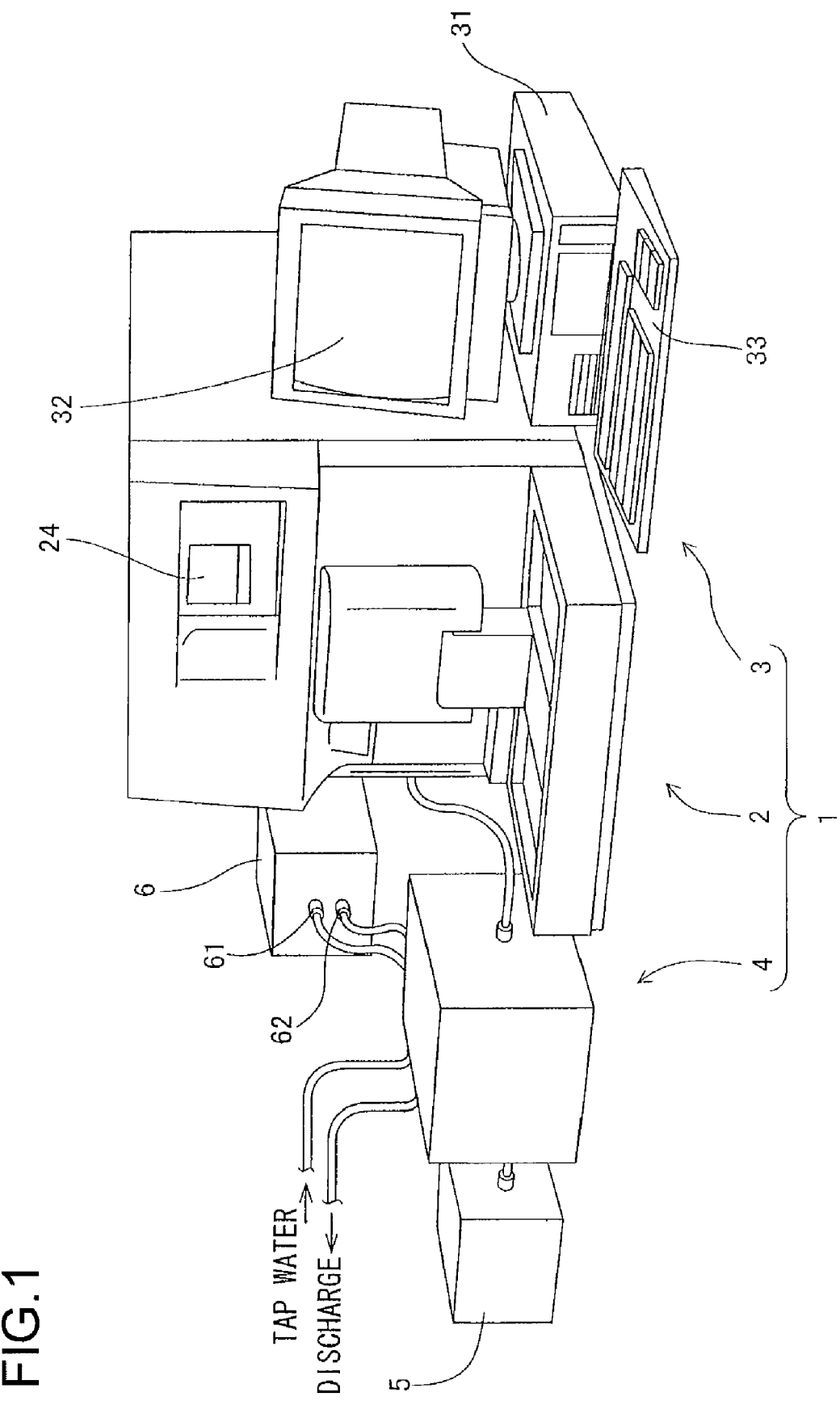
FIG. 1 is a perspective view showing a blood analysis device according to a first embodiment of the present invention.

The blood analysis device 1 according to the first embodiment of the present invention is constituted by a measurement unit 2 having a function of measuring blood which is a biological specimen, a data processing unit 3 analyzing measurement data outputted from the measurement unit 2 and obtaining results of analysis and a reagent preparation device 4 preparing a reagent employed in sample processing, as shown in FIG. 1. The measurement unit 2 is constituted to measure white blood cells, reticulocytes and blood platelets in blood by flow cytometry method. The flow cytometry method is a measurement method of particles (blood cells) detecting forward scattered light, lateral scattered light and lateral fluorescence which the particles (blood cells) emit in a measurement specimen by forming flow of a specimen including the measurement specimen and applying a laser beam to the flow of the specimen.

Figure 2:
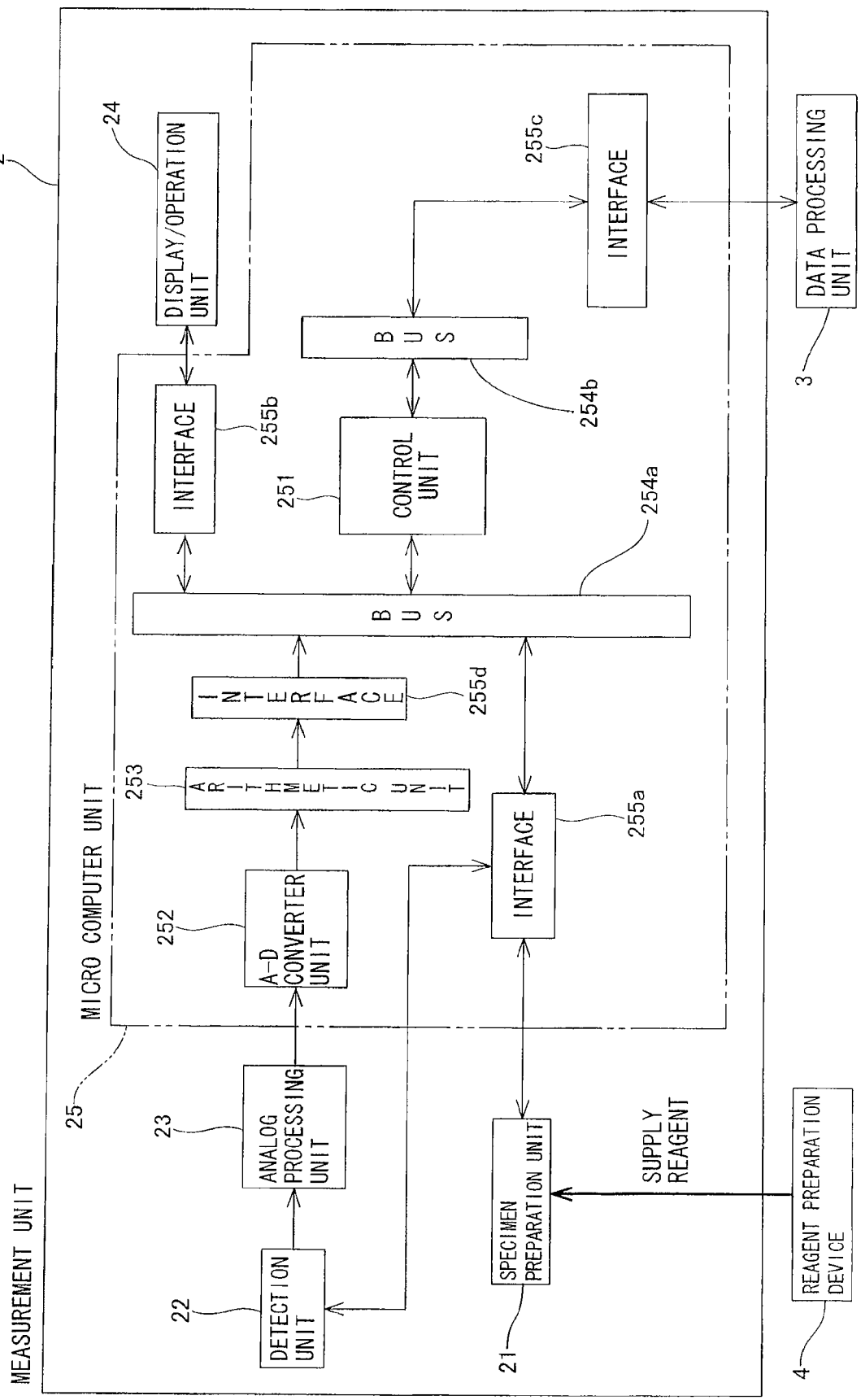
FIG. 2 is a block diagram showing a structure of the blood analysis device according to the first embodiment shown in FIG. 1.

As shown in FIG. 2, the measurement unit 2 comprises a specimen preparation unit 21, a detection unit 22 measuring a measurement specimen, an analog processing unit 23 to output of the detection unit 22, a display/operation unit 24, and a micro computer unit 25 for controlling the measurement unit 2.

Figure 3:
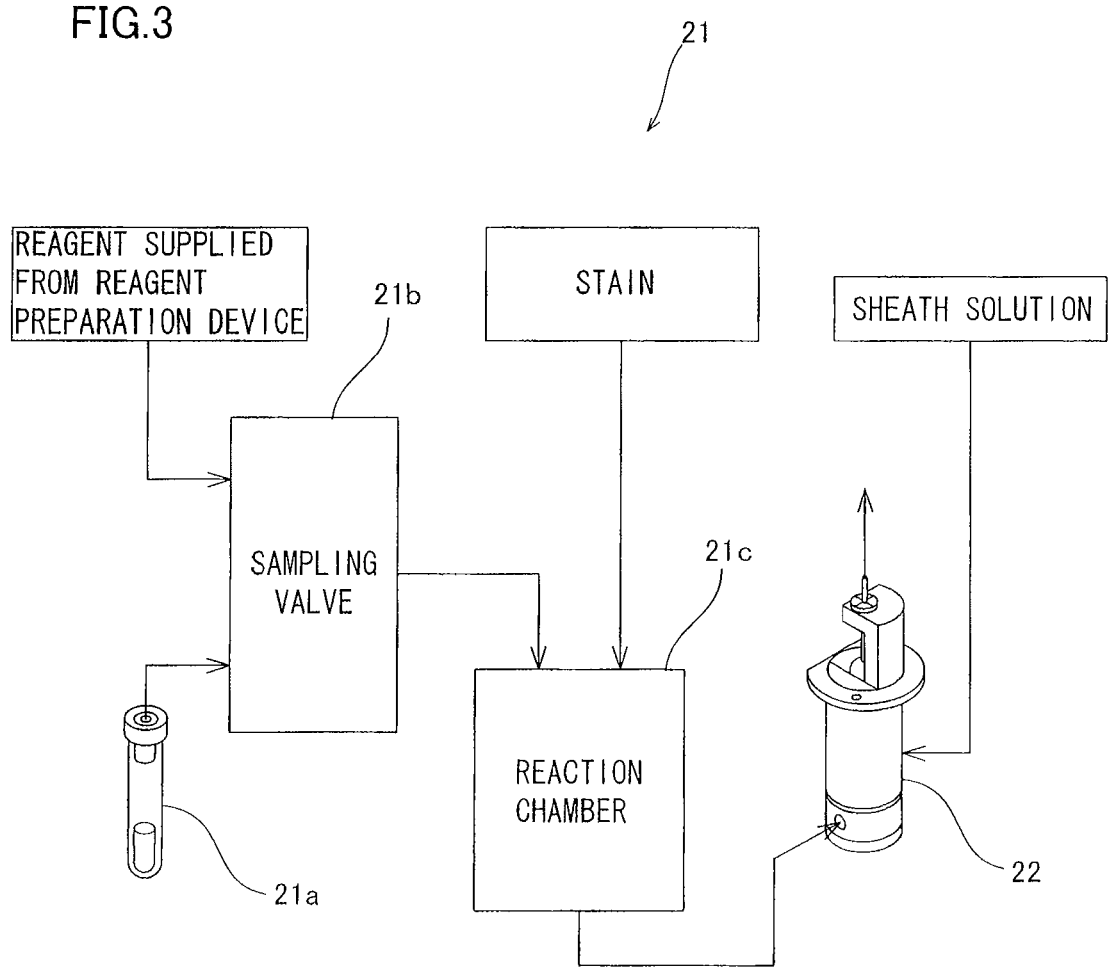
FIG. 3 is a diagram for illustrating a specimen preparation unit of the blood analysis device according to the first embodiment shown in FIG. 1.

The specimen preparation unit 21 is provided for preparing a white blood cell measurement specimen, a reticulocyte measurement specimen and a blood platelet measurement specimen. As shown in FIG. 3, the specimen preparation unit 21 includes a blood collection tube 21a filled with a prescribed amount of blood, a sampling valve 21b sucking blood and a reaction chamber 21c. The blood collection tube 21a is enabled to be replaced and exchange blood. The sampling valve 21b has a function of determining a prescribed amount of blood of the blood collection tube 21a sucked by a suction pipette (not shown). The sampling valve 21b is enabled to mix a prescribed reagent in the sucked blood. In other words, the sampling valve 21b is enabled to form a diluted specimen mixed with the prescribed amount of reagent supplied from the reagent preparation device 4 to a prescribed amount of blood. The reaction chamber 21c is formed to further mix a prescribed stain in the diluted specimen supplied from the sampling valve 21b and react the same for a prescribed time. Thus, the specimen preparation unit 21 has a function of staining white blood cells and preparing a measurement specimen of hemolyzed red blood cells as a white blood cell measurement specimen. The specimen preparation unit 21 has a function of preparing a measurement specimen stained with reticulocytes as a reticulocyte measurement specimen and preparing a measurement specimen stained with blood platelets as a blood platelet measurement specimen.

The specimen preparation unit 21 is so formed as to supply the white blood cell measurement specimen from the specimen preparation unit 21 to a sheath flow cell 22c (see FIG. 4), described later, together with a sheath solution in a white blood cell classification measurement (hereinafter referred to as a "DIFF measurement") mode. The specimen preparation unit 21 is so formed as to supply the reticulocyte measurement specimen from the specimen preparation unit 21 to the sheath flow cell 22c together with the sheath solution in a reticulocyte measurement (hereinafter referred to as a "RET measurement") mode. The specimen preparation unit 21 is so formed as to supply the blood platelet measurement specimen from the specimen preparation unit 21 to the sheath flow cell 22c together with the sheath solution in a blood platelet measurement (hereinafter referred to as a "PLT measurement") mode.

Figure 4:
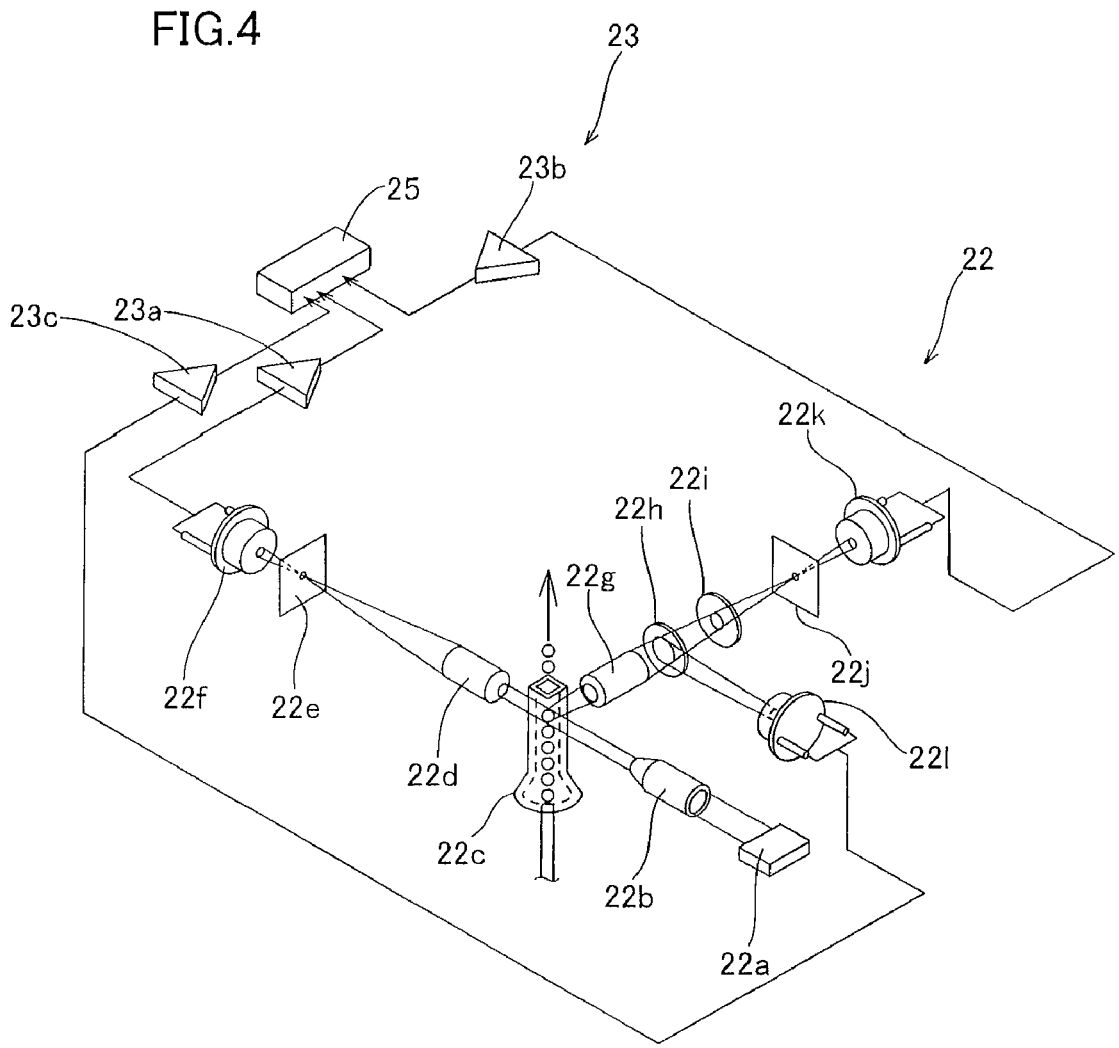
FIG. 4 is a schematic diagram showing a detection unit of the blood analysis device according to the first embodiment shown in FIG. 1.

As shown in FIG. 4, the detection unit 22 includes a light emitting unit 22a for emitting a laser beam, an illumination lens unit 22b, the sheath flow cell 22c for applying the laser beam, a condensing lens 22d, a pinhole 22e and a PD (photodiode) 22f arranged on an extension line of a traveling direction of the laser beam emitted from the light emitting unit 22a, a condensing lens 22g, a dichroic mirror 22h, an optical filter 22i, a pinhole 22j and an APD (avalanche photodiode) 22k arranged in a direction intersecting with the traveling direction of the laser beam emitted from the light emitting unit 22a, and a PD 22l arranged in a lateral direction of the dichroic mirror 22h.

The light emitting unit 22a is provided for emitting light with respect to the flow of the specimen including the measurement specimen passing through the inside of the sheath flow cell 22c. The illumination lens unit 22b is provided for parallelizing the light emitted from the light emitting unit 22a. The PD 22f is provided for receiving forward scattered light emitted from the sheath flow cell 22c. It is possible to obtain information on sizes of the particles (blood cells) in the measurement specimen by the forward scattered light emitted from the sheath flow cell 22c.

The dichroic mirror 22h is provided for separating lateral scattered light and lateral fluorescence emitted from the sheath flow cell 22c. More specifically, the dichroic mirror 22h is provided for introducing the lateral scattered light emitted from the sheath flow cell 22c into the PD 22l and introducing the lateral fluorescence emitted from the sheath flow cell 22c to the APD 22k. The PD 22l is provided for receiving the lateral scattered light. It is possible to obtain inside information such as sizes of nucleuses of the particles (blood cells) in the measurement specimen by the lateral scattered light emitted from the sheath flow cell 22c. The APD 22k is provided for receiving the lateral fluorescence. It is possible to obtain information on staining degrees of the particles (blood cells) in the measurement specimen by the lateral fluorescence emitted from the sheath flow cell 22c. The PDs 22f and 22l and the APD 22k have functions of converting the received light signals to electric signals, respectively.

As shown in FIG. 4, the analog processing unit 23 includes amplifiers 23a, 23b and 23c. The amplifiers 23a, 23b and 23c are provided for executing amplification and waveform processing for the electric signals outputted from the PDs 22f and 22l and the APD 22k, respectively.

As shown in FIG. 2, the micro computer unit 25 includes a control unit 251 having a control processor and a memory for operating the control processor, an A-D conversion unit 252 converting a signal outputted from the analog processing unit 23 to a digital signal and an arithmetic unit 253 for performing prescribed processing for the digital signal outputted from the A-D conversion unit 252. The control unit 251 has a function of controlling the specimen preparation unit 21 and the detection unit 22 through a bus 254a and an interface 255a. The control unit 251 is connected to the display/operation unit 24 through the bus 254a and an interface 255b and connected to the data processing unit 3 through a bus 254b and an interface 255c. The arithmetic unit 253 has a function of outputting an arithmetic result to the control unit 251 through an interface 255d and the bus 254a. The control unit 251 has a function transmitting the arithmetic result (measurement data) to the data processing unit 3.

Figure 5:
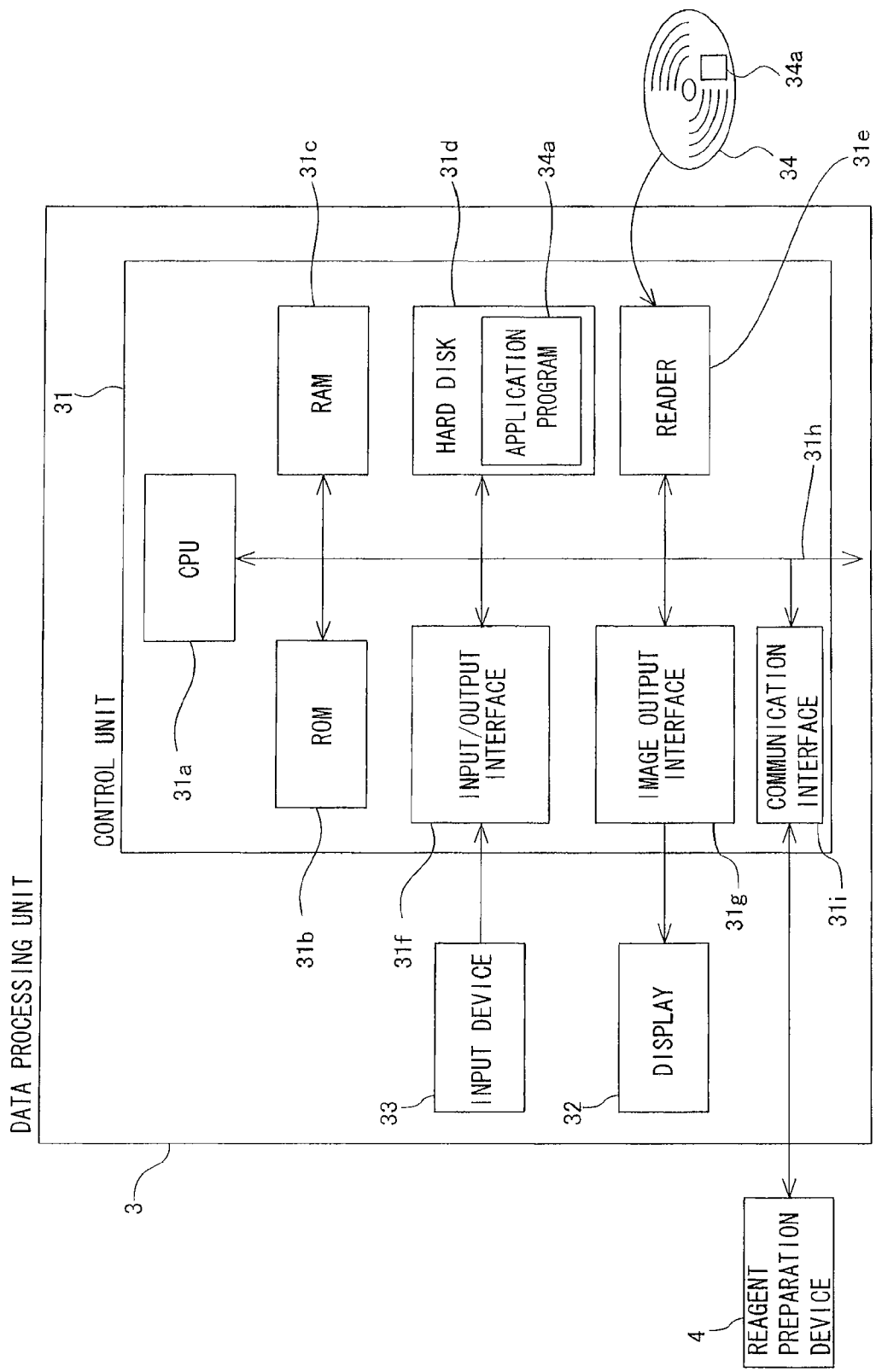
FIG. 5 is a block diagram showing a structure of a data processing unit of the blood analysis device according to the first embodiment shown in FIG. 1.

As shown in FIG. 1, the data processing unit 3 is constituted by a personal computer (PC) or the like, and has a function of analyzing the measurement data of the measurement unit 2 and displaying the results of analysis. The data processing unit 3 includes a control unit 31, a display unit 32 and an input device 33. The control unit 31 has a function of transmitting a measurement start signal including measurement mode information and a shutdown signal to the measurement unit 2. As shown in FIG. 5, the control unit 31 is constituted by a CPU 31a, an ROM 31b, a RAM 31c, a hard disk 31d, a reader 31e, an input/output interface 31f, an image output interface 31g and a communication interface 31i. The CPU 31a, the ROM 31b, the RAM 31c, the hard disk 31d, the reader 31e, the input/output interface 31f, the image output interface 31g and the communication interface 31i are connected by a bus 31h.

The CPU 31a is provided for running computer programs stored in the ROM 31b and computer programs loaded in the RAM 31c. The ROM 31b is constituted by a mask ROM, a PROM, an EPROM, an EEPROM or the like, and the computer programs run by the CPU 31a and data employed therefor are recorded therein.

The RAM 31c is constituted of an SRAM or a DRAM. The RAM 31c is employed for reading the computer programs recorded in the ROM 31b and the hard disk 31d. Further, the RAM 31c is utilized as a working area of the CPU 31a when running these computer programs.

An operating system and various computer programs such as application programs to be run by the CPU 31a as well as data employed for running the computer programs are installed in the hard disk 31d. The application program 34a described later is also installed in this hard disk 31d.

The reader 31e is constituted by a flexible disk drive, a CD-ROM drive or a DVD-ROM drive, and can read computer programs or data recorded in a portable recording medium 34. The potable recording medium 34 stores the application program 34a for execution of a prescribed function by the computer, while the computer as the data processing unit 3 can read the application program 34a from the portable recording medium 34 and install this application program 34a in the hard disk 31d.

The aforementioned application program 34a is not only provided by the portable recording medium 34, but can also be provided from an external apparatus communicably connected with the data processing unit 3 by an electric communication line (whether wire or wireless) through the aforementioned electric communication line. For example, it is also possible that the aforementioned application program 34a is stored in a hard disk of a server computer on the Internet, so that the data processing unit 3 accesses this server computer, downloads the application program 34a and installs the same in the hard disk 31d.

Further, the operating system such as Windows (registered trademark) manufactured and sold by Microsoft, U.S.A., for example, providing graphical user interface environment is installed in the hard disk 31d. In the following description, it is assumed that the application program 34a according to this embodiment operates on the aforementioned operating system.

The input interface 31f is constituted by a serial interface such as USB, IEEE 1394 or RS-232C, a parallel interface such as SCSI, IDE or IEEE 1284, an analog interface formed by a D/A converter, an A/D converter etc. or the like, for example. The input device 33 constituted by a keyboard and a mouse is connected to the input/output interface 31f, so that the user can input data into the data processing unit 3 by using this input device 33 by a user. The input device 33 has a function of accepting a measurement mode.

The image output interface 31g is connected to the display unit 32 constituted by an LCD or a CRT, for outputting an image signal corresponding to image data supplied from the CPU 31a to the display unit 32. The display unit 32 displays an image (screen) according to the inputted image signal.

The reagent preparation device 4 is provided for preparing the reagent employed in the specimen preparation unit 21 of the measurement unit 2. More specifically, the reagent preparation device 4 is so formed as to prepare a reagent employed in blood analysis by diluting the high-concentration reagent with RO water prepared from tap water as a dilution liquid. The RO water is water obtained after removing impurities by transmitting through an RO (reverse osmosis) membrane.

Figure 6:
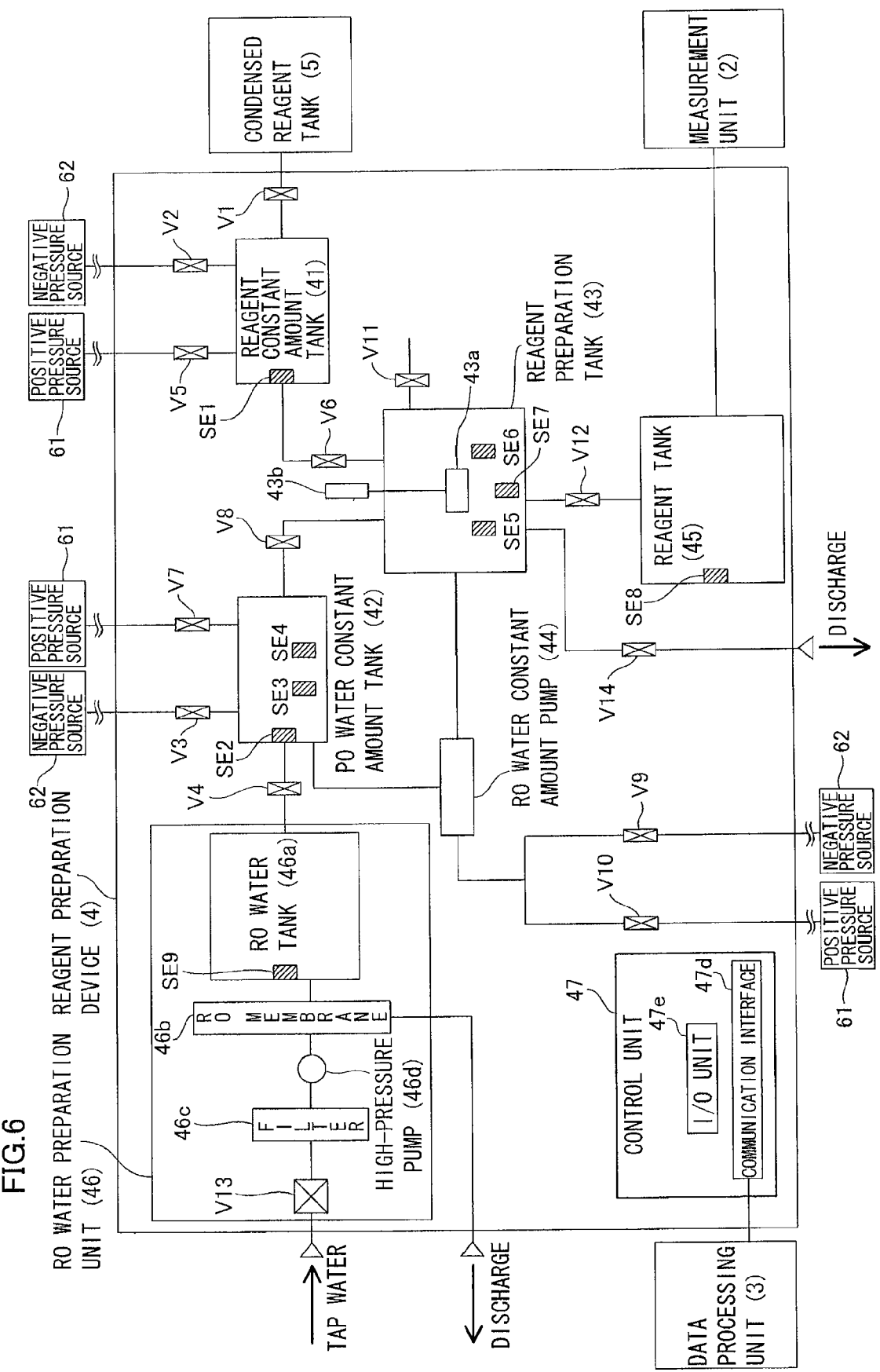
FIG. 6 is a block diagram showing a structure of a reagent preparation device of the blood analysis device according to the first embodiment shown in FIG. 1.

As shown in FIG. 6, the reagent preparation device 4 includes a reagent constant amount tank 41 for quantifying and supplying the high-concentration reagent from a high-concentration reagent tank 5 storing the high-concentration reagent, an RO water constant amount tank 42 quantifying and supplying the RO water for diluting the high-concentration reagent, a reagent preparation tank 43 storing the high-concentration reagent and the RO water and preparing the reagent employed in blood analysis, an RO water constant amount pump (diaphragm pump) 44, a reagent tank 45 for storing the prepared reagent, an RO water preparation unit 46 preparing the RO water from the tap water, and a control unit 47 controlling an operation of the reagent preparation device 4.

A pneumatic device 6 (see FIG. 1) including positive pressure sources 61 applying positive pressures and negative pressure sources 62 applying negative pressures is provided on an outer portion of the reagent preparation device 4 in order to control movement of each liquid in the device. The positive pressure sources 61 and the negative pressure sources 62 are connected to respective prescribed portions of the reagent preparation device 4.

The reagent constant amount tank 41 is provided with a liquid level sensor SE1 for detecting the amount of the high-concentration reagent in the tank. The reagent constant amount tank 41 is connected to the high-concentration reagent tank 5 through an electromagnetic valve V1, and connected to the negative pressure source 62 through an electromagnetic valve V2. The electromagnetic valves V1 and V2 are opened, thereby applying a negative pressure to the reagent constant amount tank 41 and supplying the high-concentration reagent from the high-concentration reagent tank 5 to the reagent constant amount tank 41. When the liquid level sensor SE1 has detected that the high-concentration reagent reaches a prescribed amount, the electromagnetic valves V1 and V2 are closed to stop the supply of the high-concentration reagent. Thus, the prescribed amount of high-concentration reagent is determined.

The RO water constant amount tank 42 is provided with a liquid level sensor SE2 for detecting the amount of the RO water in the tank, a conductivity sensor SE3 detecting an electrical conductance of the RO water in the tank, and a temperature sensor SE4 measuring a temperature of the RO water in the tank. The RO water constant amount tank 42 is connected to the negative pressure source 62 through an electromagnetic valve V3, and connected to an RO water tank 46a of the RO water preparation unit 46, described later, through an electromagnetic valve V4. The electromagnetic valves V3 and V4 are opened, thereby applying a negative pressure to the RO water constant amount tank 42 and supplying the RO water from the RO water tank 46a to the RO water constant amount tank 42. When the liquid level sensor SE2 is detected that the RO water has reached a prescribed amount, the electromagnetic valves V3 and V4 are closed to stop the supply of the RO water. Thus, the prescribed amount of RO water is determined.

The reagent constant amount tank 41 is connected to the positive pressure source 61 through an electromagnetic valve V5, and the reagent constant amount tank 41 and the reagent preparation tank 43 are connected to each other through an electromagnetic valve V6. The electromagnetic valves V5 and V6 are opened, thereby applying a positive pressure to the reagent constant amount tank 41 and supplying the prescribed amount of high-concentration reagent from the reagent constant amount tank 41 to the reagent preparation tank 43. The electromagnetic valves V5 and V6 are closed after the high-concentration reagent in the reagent constant amount tank 41 is supplied to the reagent preparation tank 43. The RO water constant amount tank 42 is connected to the positive pressure source 61 through an electromagnetic valve V7, and the RO water constant amount tank 42 and the reagent preparation tank 43 are connected to each other through an electromagnetic valve V8. The electromagnetic valves V7 and V8 are opened, thereby applying a positive pressure to the RO water constant amount tank 42 and supplying the prescribed amount of RO water from the RO water constant amount tank 42 to the reagent preparation tank 43. The electromagnetic valves V7 and V8 are closed after the RO water in the RO water constant amount tank 42 is supplied to the reagent preparation tank 43.

The reagent preparation device 4 is so formed that the high-concentration reagent is diluted by 25 times by the RO water in the reagent preparation tank 43. More specifically, the RO water is supplied from the RO water constant amount tank 42 to the reagent preparation tank 43 and the high-concentration reagent is supplied from the reagent constant amount tank 41 to the reagent preparation tank 43 so that the mixing ratio of the high-concentration reagent and the RO water in the reagent preparation tank 43 is 1:24 (dilution magnification: 25 times).

The reagent preparation tank 43 is provided with a stirring unit 43a mixing and stirring the supplied high-concentration reagent and RO water, and the stirring unit 43a is driven by a motor 43b. The reagent preparation tank 43 is further provided with two conductivity sensors SE 5 and SE6 detecting the electrical conductance of the reagent obtained by mixing and stirring the high-concentration reagent and the RO water by the stirring unit 43a, and a temperature sensor SE7 measuring the temperature of the reagent obtained by mixing and stirring the high-concentration reagent and the RO water by the stirring unit 43a. The conductivity sensors SE 5 and SE6 are arranged on respective different positions in the reagent preparation tank 43.

The RO water constant amount pump (diaphragm pump) 44 has a function of discharging the RO water, and is enabled to gradually supply the prescribed amount of RO water to the reagent preparation tank 43 in order to dilute the reagent in the reagent preparation tank 43 at a desired concentration.

The RO water constant amount pump 44 is connected to the negative pressure source 62 through an electromagnetic valve V9. The electromagnetic valves V7 and V9 are opened, thereby applying a negative pressure to the RO water constant amount pump 44, applying a positive pressure to the RO water constant amount tank 42, and supplying the RO water from the RO water constant amount tank 42 to the RO water constant amount pump 44. The RO water constant amount pump 44 is connected also to the positive pressure source 61 through an electromagnetic valve V10, and the reagent preparation tank 43 is provided with an electromagnetic valve V11 so as to open to the atmosphere. The electromagnetic valves V10 and V11 are opened, thereby applying a positive pressure to the RO water constant amount pump 44 and supplying the prescribed amount of RO water from the RO water constant amount pump 44 to the reagent preparation tank 43.

The reagent preparation tank 43 and the reagent tank 45 are connected to each other through an electromagnetic valve V12. The electromagnetic valves V11 and V12 are opened, so that a pressure in the reagent preparation tank 43 is opened to the atmosphere and the reagent diluted at the desired concentration is supplied from the reagent preparation tank 43 to the reagent tank 45 provided below the reagent preparation tank 43. The reagent tank 45 is provided with a liquid level sensor SE8 for detecting the amount of the reagent in the tank. The control unit 47 determines whether or not the reagent is newly prepared at a desired concentration on the basis of a detection result of the liquid level sensor SE8. The reagent tank 45 is connected to the measurement unit 2 and is enabled to supply the reagent in the reagent preparation tank 45 to the measurement unit 2.

The RO water preparation unit 46 is enabled to prepare the RO water as the dilution liquid for diluting the high-concentration reagent with the tap water. Thus, no device for preparing the RO water other than the reagent preparation device 4 may be separately provided. The RO water preparation unit 46 includes the RO water tank 46a, an RO membrane 46b, a filter 46c protecting the RO membrane 46b by removing impurities containing the tap water, a high-pressure pump 46d applying a high pressure to water passing through the filter 46c so as to transmit water molecules through the RO membrane 46b, and an electromagnetic valve V13 controlling supply of the tap water.

The RO water tank 46a is provided for storing the RO water transmitted through the RO membrane 46b. The RO water tank 46a is provided with a liquid level sensor SE9 for detecting the amount of RO water in the tank, and the RO water is prepared on the basis of a detection result of the liquid level sensor SE9. Thus, a prescribed amount of RO water can be always ensured in the RO water tank 46a. In a series of flow of RO water preparation, the electromagnetic valve V13 is first opened and the tap water reaches the filter 46c. The water transmitted through the filter 46c is applied with a pressure by the high-pressure pump 46d to transmit the water through the RO membrane 46b, and RO water transmitted through the RO membrane 46b is supplied to the storage tank 46a. Water containing impurities, not transmitted through the RO membrane 46b is discharged outside the reagent preparation device 4.

Figure 7:
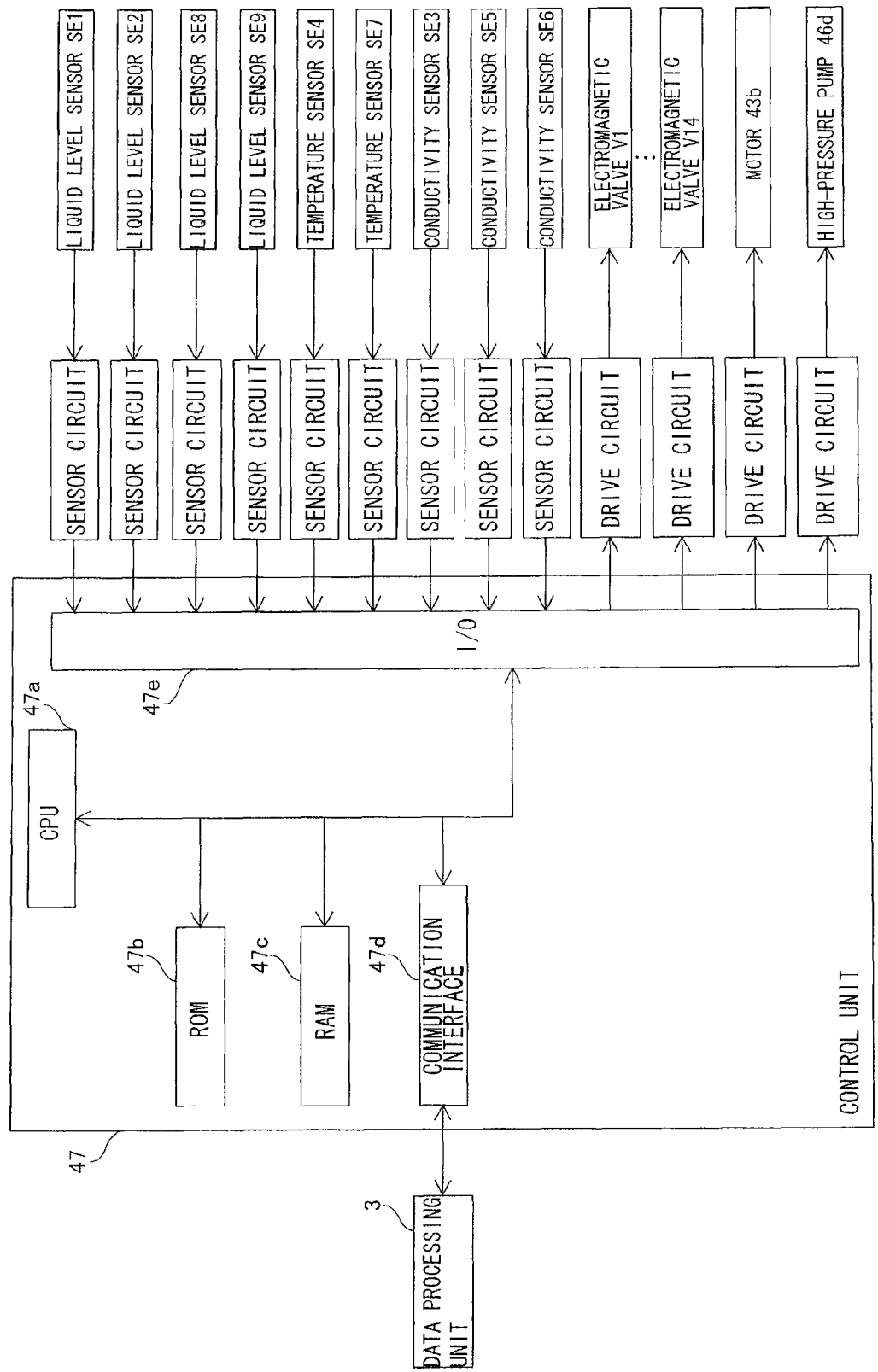
FIG. 7 is a block diagram for illustrating a control unit of a reagent preparation device of the blood analysis device according to the first embodiment of the present invention.

As shown in FIG. 7, the control unit 47 includes a CPU 47a, an ROM 47b, a RAM 47c, and a communication interface 47d connected to the data processing unit 3, and an I/O (input/output) unit 47e connected to respective portions in the reagent preparation device 4.

The CPU 47a is provided for running computer programs stored in the ROM 47b and computer programs loaded in the RAM 47c. Further, the RAM 47c is utilized as a working area of the CPU 47a when running these computer programs.

In the first embodiment, the CPU 47a detects the electrical conductance of the RO water in the RO water constant amount tank 42 by the conductivity sensor SE3 and stores a detection value Y1 in the RAM 47c. The CPU 47a is so formed as to measure the temperature of the RO water in the RO water constant amount tank 42 by the temperature sensor SE4 and also store a measurement value T1 in the RAM 47c.

The CPU 47a so drives the stirring unit 43a by the motor 43b that a detection value YS5 detected by a conductivity sensor SE5 provided in the reagent preparation tank 43 and a detection value YS6 detected by the conductivity sensor SE6 are substantially the same. More specifically, the CPU 47a determines whether or not an absolute value |YS5−YS6| of difference between the two detection values is smaller than a prescribed value M, and so drives the stirring unit 43a with the motor 43b that the absolute value is smaller than the prescribed value M. Thus, it is possible to suppress dispersion of the electrical conductance of the reagent detected in the reagent preparation tank 43 depending on a position of the conductivity sensor. When the absolute value |YS5−YS6| is smaller than the prescribed value M, the CPU 47a detects the electrical conductance of the reagent in the reagent preparation tank 43 with the conductivity sensor SE5, and stores a detection value Y2 at that time in the RAM 47c. At this time, the CPU 47a also measures the temperature of the reagent in the reagent preparation tank 43 with the temperature sensor SE7, and stores a measurement value T2 in the RAM 47c.

The CPU 47a so supplies the RO water to the reagent preparation tank 43 with the RO water constant amount tank 42 (also with the RO water constant amount pump 44, if necessary) that the detection value Y2 by the conductivity sensor SE5 is in a prescribed range with respect to a target value Z of an electrical conductance for diluting the high-concentration reagent at the desired concentration. The general formula for obtaining the target value of the electrical conductance of the reagent is expressed by the following formula (1):

$$Z_0 = \{X+(A-1)Y\}/A \quad (1)$$

In the aforementioned formula (1), $Z_0$ represents a target value (ms/cm) of an electrical conductance at 25° C. of the reagent obtained by mixing and stirring the high-concentration reagent and the RO water, X represents an electrical conductance (ms/cm) at 25° C. of the high-concentration reagent, Y represents an electrical conductance (ms/cm) at 25° C. of the RO water, and A represents a (known) dilution magnification (25 times in the first embodiment). The X is a value inherent to the high-concentration reagent and a known value previously obtained by an experiment or the like.

A compensation formula for considering the temperature of the RO water and change in the temperature of the reagent obtained by mixing and stirring the high-concentration reagent and the RO water is expressed by the following formula (2):

$$Z = [\{X+(A-1)Y\}/A] \times \{1+\alpha 1(T2-25)\} = [[X+(A-1)Y1/\{1+\alpha 0(T1-25)\}]/A] \times \{1+\alpha 1(T2-25)\} \quad (2)$$

In the aforementioned formula (2), Z represents a target value (ms/cm) of an electrical conductance at T2° C. of the reagent obtained by mixing and stirring the high-concentration reagent and the RO water, Y1 represents an electrical conductance (ms/cm) at T1° C. of the RO water, T1 is a temperature (° C.) of the RO water, T2 is a temperature (° C.) of the reagent obtained by mixing and stirring the high-concentration reagent and the RO water, $\alpha 0$ represents a temperature coefficient with respect to 25° C. of the electrical conductance of the RO water, $\alpha 1$ represents a temperature coefficient with respect to 25° C. of the electrical conductance of the reagent obtained by mixing and stirring the high-concentration reagent and the RO water. 0.02 is simply employed as the temperature coefficients $\alpha 0$ and $\alpha 1$ in JIS (Japanese Industrial Standards) while they varies according to kinds or a concentration of a liquid.

In the first embodiment, the CPU 47a is formed to calculate the target value Z by the aforementioned formula (2). Therefore, the CPU 47a decides the target value on the basis of the desirable (known) dilution magnification A, the detection value Y1 of the electrical conductance of the RO water, the measurement value T1 of the temperature of the RO water, the measurement value T2 of the temperature of the mixed and stirred reagent and the (known) electrical conductance X of the high-concentration reagent.

The communication interface 47d is enabled to transmit error information to the data processing unit 3 so that a user can easily recognize an error caused in the reagent preparation device 4. An error notification is displayed on the display unit 32 of the data processing unit 3 on the basis of this error information.

The I/O unit 47e is so formed that signals are inputted from the respective sensor SE1 to S9 through the respective sensor circuits, as shown in FIG. 7. The I/O unit 47e is so formed as to output signals of respective drive circuits in order to control drive of the electromagnetic valves V1 to V13, the motor 43b and the high-pressure pump 46d through the respective drive circuits.

A reagent preparation processing operation of the blood analysis device 1 according to the first embodiment of the present invention will be now described with reference to FIGS. 6 and 8.

Figure 8:
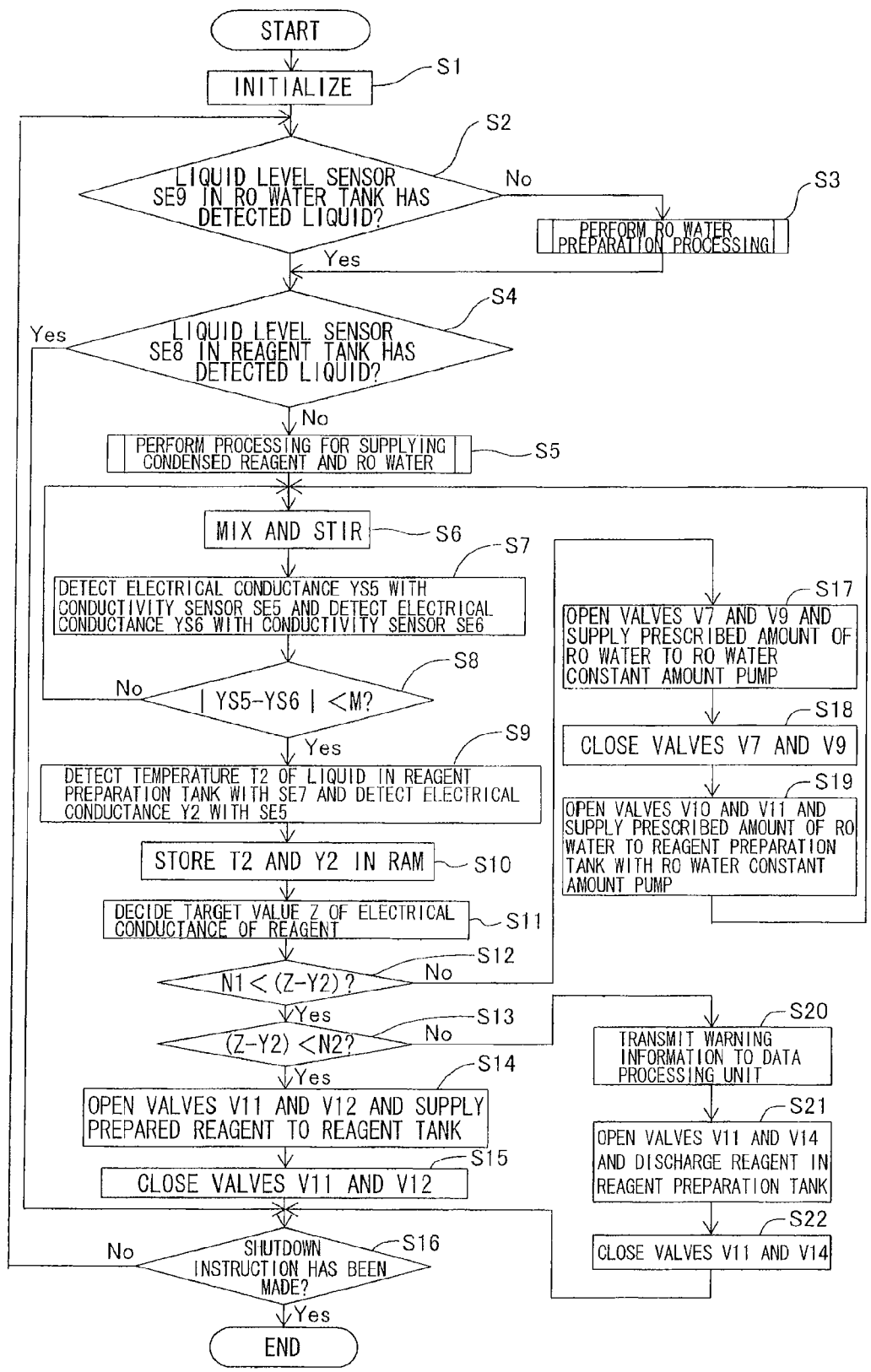
FIG. 8 is a flow chart for illustrating a reagent preparation processing operation of the blood analysis device according to the first embodiment of the present invention.

At a step S1 in FIG. 8, the CPU 47a first initializes the computer programs stored in the ROM 47b. At a step S2, the CPU 47a determines whether or not the liquid level sensor SE9 provided in the RO water tank 46a has detected a liquid. If the liquid level sensor SE9 has not detected the liquid, namely, if the prescribed amount of RO water is not stored in the RO water tank 46a, the CPU 47a performs RO water preparation processing with the RO water preparation unit 46 at a step S3. The RO water preparation processing at the step S3 will be described later. If the liquid level sensor SE9 has detected the liquid, the CPU 47a determines whether or not the liquid level sensor SE8 of the reagent tank 45 has detected at a step S4. If the liquid level sensor SE8 has detected the liquid, namely, if the prescribed amount of reagent is stored in the reagent tank 45, the prescribed amount of reagent for using in the measurement unit 2 is ensured, and hence the process advances to a step S15 without newly preparing a reagent. If the liquid level sensor SE8 has not detected the liquid, the CPU 47a performs processing for supplying the high-concentration reagent and the RO water to the reagent preparation tank 43 at a step S5 in order to newly prepare the reagent. The processing for supplying the high-concentration reagent and the RO water at the step S5 will be described later.

At a step S6, the CPU 47a mixes and stirs the high-concentration reagent and the RO water supplied to the reagent preparation tank 43 with the stirring unit 43a. At a step S7, the CPU 47a detects the electrical conductance YS5 of the reagent in the reagent preparation tank 43 with the conductivity sensor SE5, and detects the electrical conductance YS6 of the reagent in the reagent preparation tank 43 with the conductivity sensor SE6. At a step S8, the CPU 47a determines whether or not the absolute value |YS5−YS6| which is the difference between the detection values YS5 and YS6 is smaller than the prescribed value M. If it is not smaller than the prescribed value M, the electrical conductance by the detection position varies, and hence stirring by the stirring unit 43a is repeated. If the absolute value |YS5−YS6| is smaller than the prescribed value M, the CPU 47a measures the temperature T2 of the reagent in the reagent preparation tank 43 at that time with the temperature sensor SE7, and detects the electrical conductance Y2 of the reagent with the conductivity sensor SE5 at a step S9.

The CPU 47a stores the measurement value T2 and the detection value Y2 in the RAM 47c at a step S10, and the target value Z of the electrical conductance of the reagent in the reagent preparation tank 43 is calculated by the aforementioned formula (2) at a step S11. At a step S12, the CPU 47a determines whether or not difference between the target value Z and the detection value Y2 (Z−Y2) is larger than a prescribed value N1 (negative value). If the difference (Z−Y2) is smaller than the prescribed value N1, the RO water must be further supplied to the reagent preparation tank 43, and hence the electromagnetic valves V7 and V9 are opened in order to supply the RO water to the RO water constant amount pump 44 at a step S17. After supplying the RO water to the RO water constant amount pump 44, the CPU 47a closes the electromagnetic valves V7 and V9 at a step S18 and opens the electromagnetic valves V10 and V11 at a step S19, so that the prescribed amount of RO water is additionally supplied from the RO water constant amount pump 44 to the reagent preparation tank 43. The electrical conductance of the reagent in the reagent preparation tank 43 varies due to additional supply of the RO water, and hence the process advances to the step S6, and mixing and stirring are performed again.

If the difference (Z−Y2) is larger than the prescribed value N1 (negative value), the CPU 47a determines whether or not the difference (Z−Y2) is smaller than a prescribed value N2 at the step S13. If the difference (Z−Y2) is larger than the prescribed value N2, the concentration of the reagent in the reagent preparation tank 43 is lower than the desired concentration, and hence the CPU 47a transmits warning information showing that the reagent with the desired concentration has not been prepared to the data processing unit 3 through the communication interface 47d at a step S20. When the CPU 31a of the data processing unit 3 has received the aforementioned warning information through the communication interface 31i, a massage that the reagent with the desired concentration has not been prepared in the reagent preparation device 4 is displayed on the display unit 32. Thus, the user can easily know that the reagent has not been prepared at the desired concentration. At a step S21, the CPU 47a opens the electromagnetic valves V11 and V14 to discharge the reagent in the reagent preparation tank 43 outside the reagent preparation device 4. When the reagent in the reagent preparation tank 43 is discharged outside the reagent preparation device 4, the CPU 47a closes the electromagnetic valves V11 and V14 at a step S22.

If the difference (Z−Y2) is smaller than the prescribed value N2, the CPU 47a opens the electromagnetic valves V11 and V12 and the reagent prepared to have the electrical conductance which is substantially the same as the target value Z is supplied to the reagent tank 45 at a step S14. In other words, the reagent diluted at the desired concentration is stored in the reagent tank 45. After supplying all of the reagent in the reagent preparation tank 43 to the reagent tank 45, the CPU 47a closes the electromagnetic valves V11 and V12 at the step S15 and determines whether or not a shutdown instruction of the reagent preparation device 4 has been made at a step S16. If the shutdown instruction has been made, an operation of the reagent preparation device 4 ends. If the shutdown instruction has not been made, the process advances to the step S2.

The RO water preparation processing operation at the step S3 of the reagent preparation processing operation shown in FIG. 8 will be now described with reference to FIGS. 6 and 9.

Figure 9:
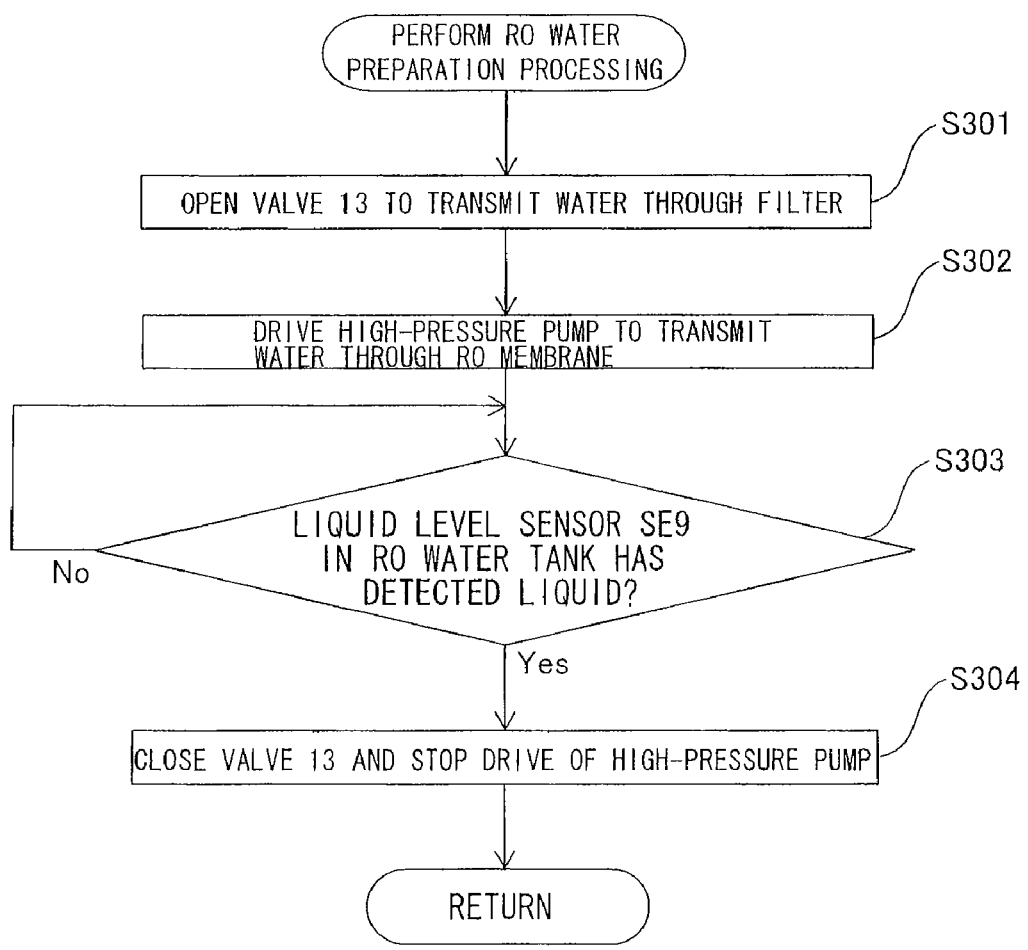
FIG. 9 is a flow chart for illustrating an RO water preparation processing operation at a step S3 of the reagent preparation processing operation shown in FIG. 8.

The CPU 47a opens the electromagnetic valve V13 to transmit the tap water through the filter 46c at a step S301 in FIG. 9. At a step S302, the CPU 47a drives the high-pressure pump 46d to transmit the water transmitted through the filter 46c through the RO membrane 46b by a high pressure. At a step S303, the CPU 47a determines whether or not the liquid level sensor SE9 of the RO water tank 46a has detected the liquid. In other words, the CPU 47a determines whether or not the prescribed amount RO water is stored in the RO water tank 46a. If the liquid level sensor SE9 has not detected the liquid, this determination is repeated, and the RO water transmitted through the RO membrane 46b is continuously supplied to the RO water tank 46a. On the other hand, if the liquid level sensor SE9 has detected the liquid, the CPU 47a closes the electromagnetic valve V13, stops the drive of the high-pressure pump 46d, and ends the operation at a step S304.

A supply processing operation of the high-concentration reagent and the RO water to the reagent preparation tank 43 at the step S5 of the reagent preparation processing operation shown in FIG. 8 will be now described with reference to FIGS. 6 and 10.

Figure 10:
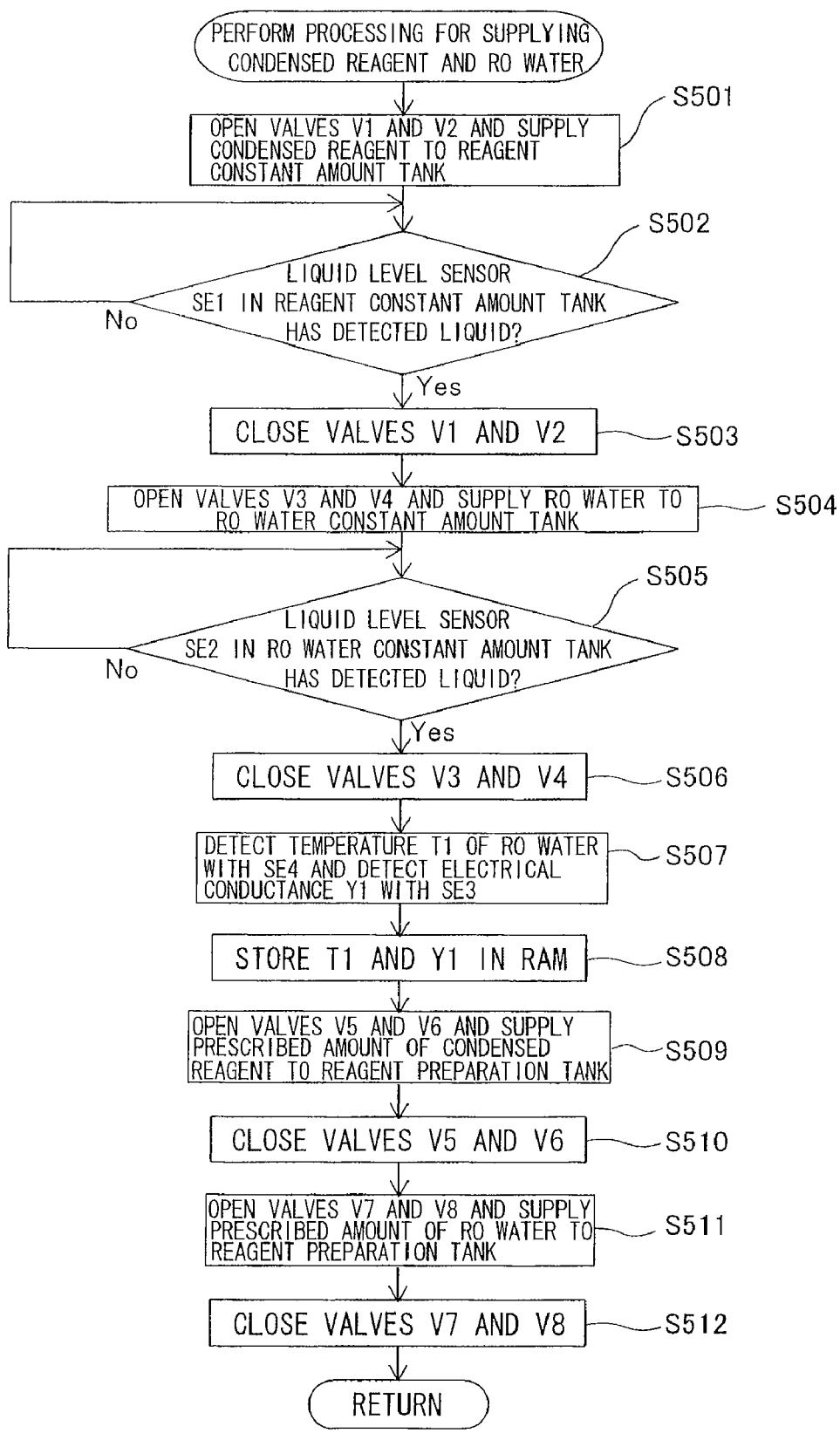
FIG. 10 is a flow chart for illustrating a supply processing operation of a high-concentration reagent and RO water to the reagent preparation tank at a step S5 of the reagent preparation processing operation shown in FIG. 8.

The CPU 47a opens the electromagnetic valves V1 and V2 and the high-concentration reagent is supplied from the high-concentration reagent tank 5 to the reagent constant amount tank 41 at a step S501 in FIG. 10. At a step S502, the CPU 47a determines whether or not the liquid level sensor SE1 of the reagent constant amount tank 41 has detected the liquid. In other words, the CPU 47a determines whether or not the prescribed amount of high-concentration reagent has been supplied to the reagent constant amount tank 41. If the liquid level sensor SE1 has not detected the liquid, this determination is repeated until the liquid level sensor SE1 detects the liquid. On the other hand, if the high-concentration reagent reaches the prescribed amount and the liquid level sensor SE1 has detected the liquid, the CPU 47a closes the electromagnetic valves V1 and V2 in order to stop the supply of the high-concentration reagent from the high-concentration reagent tank 5 at a step S503.

At a step S504, the CPU 47a opens the electromagnetic valves V3 and V4, and the RO water is supplied from the RO water tank 46a to the RO water constant amount tank 42. At a step S505, the CPU 47a determines whether or not the liquid level sensor SE2 of the RO water constant amount tank 42 has detected the liquid. In other words, the CPU 47a determines whether or not the prescribed amount of RO water has been supplied to the RO water constant amount tank 42. If the liquid level sensor SE2 has not been detected the liquid, the RO water is continuously supplied to the RO water constant amount tank 42 until the liquid level sensor SE2 detects the liquid. If the liquid level sensor SE2 has detected the liquid by supplying the prescribed amount of RO water, the CPU 47a closes the electromagnetic valves V3 and V4 and the supply from the RO water tank 46a to the RO water constant amount tank 42 ends at a step S506. At a step S507, the CPU 47a measures the temperature T1 of the RO water in the RO water constant amount tank 42 with the temperature sensor SE4, and detects the electrical conductance Y1 of the RO water with the conductivity sensor SE3. At a step S508, the CPU 47a stores the aforementioned measurement value T1 and detection value Y1 in the RAM 47c.

The CPU 47a opens the electromagnetic valves V5 and V6 and supplies the prescribed amount of high-concentration reagent from the reagent constant amount tank 41 to the reagent preparation tank 43 at a step S509, and the electromagnetic valves V5 and V6 are closed at a step S510. Aster the CPU 47a opens the electromagnetic valves V7 and V8 and supplies the prescribed amount of RO water from the RO water constant amount tank 42 to the reagent preparation tank 43 at a step S511, the CPU 47a closes the electromagnetic valves V7 and V8 at a step S512, and the operation ends.

According to the first embodiment, as hereinabove described, the control unit 47 decides the target value Z of the electrical conductance of the reagent obtained by mixing and stirring the high-concentration reagent and the RO water on the basis of the detection value Y1 detected by the conductivity sensor SE3 detecting the electrical conductance of the RO water, and so controls the supply operation of the RO water constant amount pump 44 that the detection value Y2 detected by the conductivity sensor SE5 detecting the electrical conductance of the reagent obtained by mixing and stirring the high-concentration reagent and the RO water approaches the target value Z. Thus, the target value Z is decided on the basis of a varied value also when the electrical conductance of the RO water varies, and the electrical conductance of the reagent obtained by mixing and stirring the high-concentration reagent and the RO water can approach the target value Z. Consequently, the high-concentration reagent can be diluted at the desired concentration.

According to the first embodiment, the blood analysis device 1 is provided with the conductivity sensor SE3 detecting the electrical conductance of the RO water, the temperature sensor SE4 measuring the temperature of the RO water, the conductivity sensor SE5 detecting the electrical conductance of the reagent obtained by mixing and stirring the high-concentration reagent and the RO water, and the temperature sensor SE7 measuring the temperature of the reagent obtained by mixing and stirring the high-concentration reagent and the RO water, and the control unit 47 decides the target value Z of the electrical conductance of the reagent obtained by mixing and stirring the high-concentration reagent and the RO water on the basis of the (known) desired dilution magnification A, the detection value Y1 detected by the conductivity sensor SE3, the measurement value T1 measured by the temperature sensor SE4, and the measurement value T2 measured by the temperature sensor SE7 and the (known) electrical conductance X of the high-concentration reagent. Thus, the target value Z of the electrical conductance of the reagent obtained by mixing and stirring the high-concentration reagent and the RO water is decided on the basis of not only the electrical conductance Y1 of the RO water but also the temperatures T1 and T2 correlated with the electrical conductance, and hence the high-concentration reagent can be precisely diluted at the desired concentration.

According to the first embodiment, the control unit 47 so controls the supply operation of the RO water constant amount pump 44 that a smaller amount of the RO water than the mixing amount on the basis of the mixing ratio (1:24) among the high-concentration reagent and the RO water is supplied to the reagent preparation tank 43 and the RO water is additionally gradually supplied to the reagent preparation tank 43 so as for the detection value Y2 detected by the conductivity sensor SE5 to approach the target value Z, whereby the amount of change of the electrical conductance of the reagent in the reagent preparation tank 43 can be reduced as compared with a case where the high-concentration reagent is additionally gradually supplied. Thus, the electrical conductance Y2 of the reagent in the reagent preparation tank 43, detected by the conductivity sensor SE5 can precisely approach the target value Z while changing the amount of the electrical conductance Y2 little by little.

Second Embodiment

A blood analysis device 100 according to a second embodiment of the present invention will be now described with reference to FIGS. 12 and 13. The blood analysis device 100 according to the second embodiment is so formed that information on maintenance of a reagent preparation device 104, information on a state of reagent preparation or the like is displayed on a display unit 32 of a data processing unit 3 dissimilarly to the aforementioned blood analysis device 1 according to the first embodiment. In the second embodiment, a case where the present invention is applied to the blood analysis device 100 which is an exemplary sample analysis system will be described.

Figure 12:
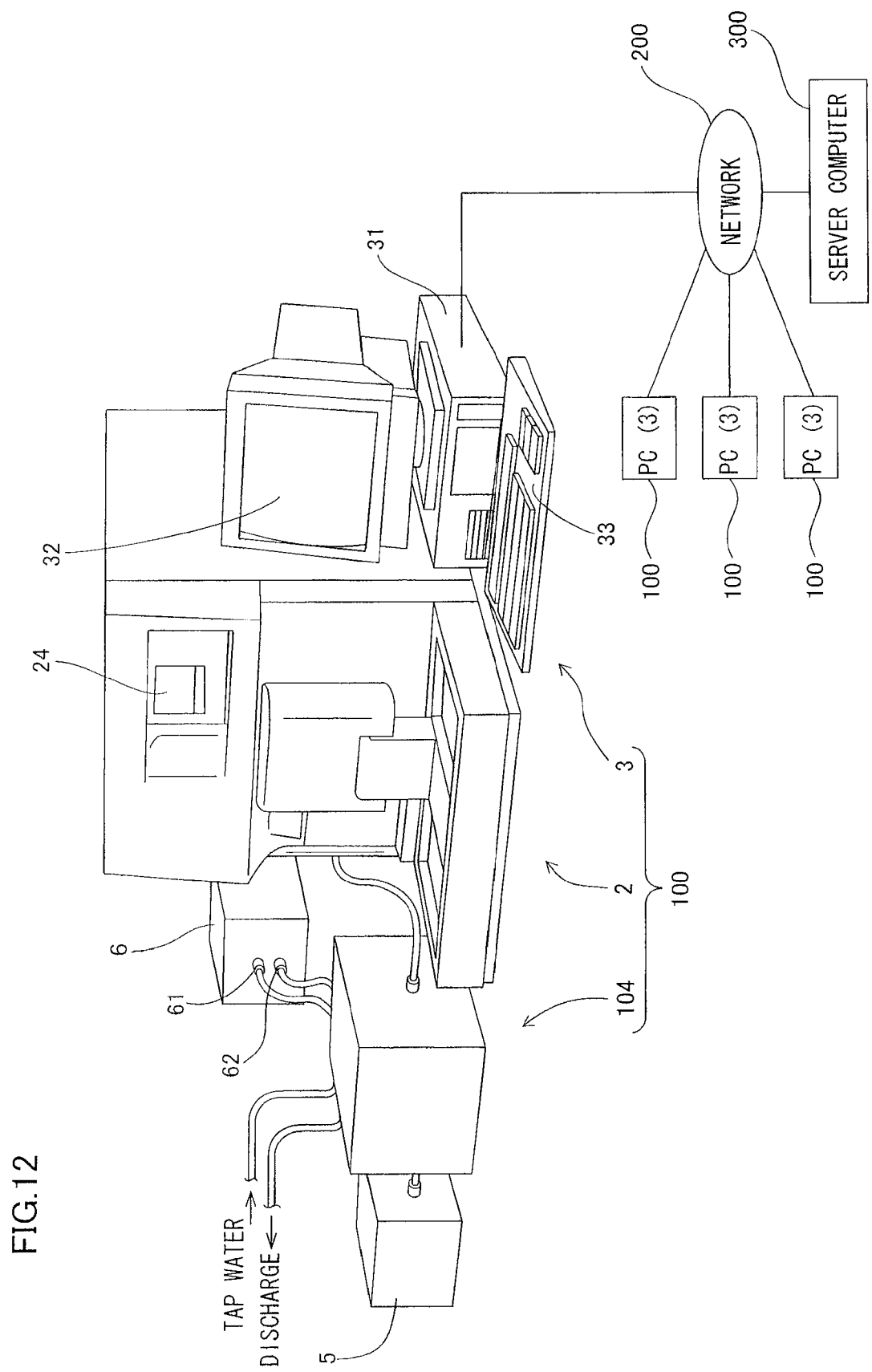
FIG. 12 is a perspective view showing a blood analysis device according to a second embodiment of the present invention.

The blood analysis device 100 according to the second embodiment is constituted by a measurement unit 2, the data processing unit 3 and the reagent preparation device 104, as shown in FIG. 12.

The data processing unit 3 has a communication interface 31i connected to a server computer 300 through a network 200. The data processing units 3 of a plurality of the blood analysis devices 100 are connected to the server computer 300 through the network 200.

Figure 13:
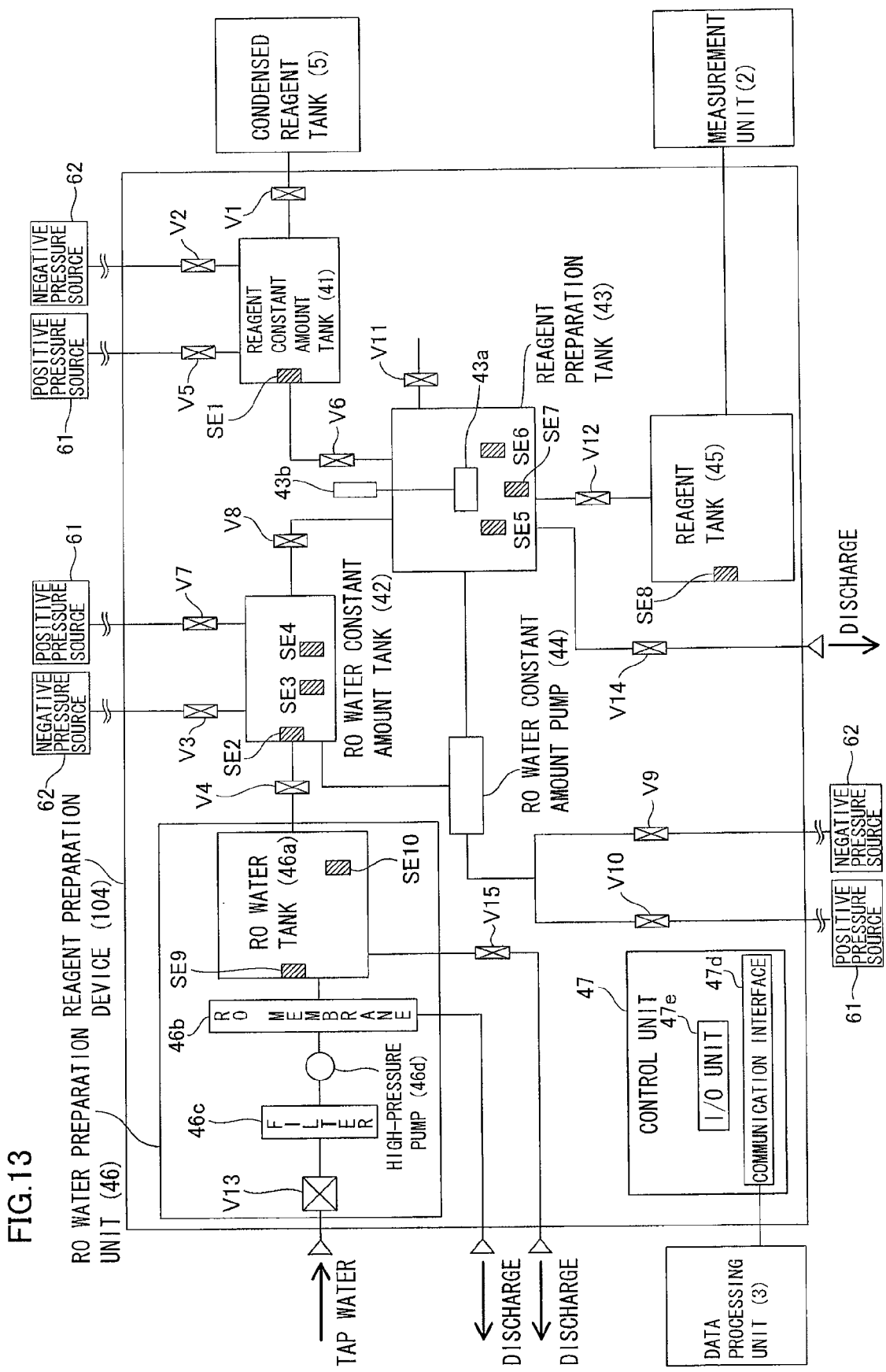
FIG. 13 is a block diagram showing a structure of a reagent preparation device of the blood analysis device according to the second embodiment of the present invention.

The reagent preparation device 104 is provided with a conductivity sensor SE10 detecting an electrical conductance of RO water to an RO water tank 46a in addition to a structure of a reagent preparation device 4 of the aforementioned first embodiment, as shown in FIG. 13. The RO water tank 46a is enabled to discharge the RO water in the tank through an electromagnetic valve V15.

A reagent preparation processing operation of the blood analysis device 100 according to the second embodiment of the present invention will be now described with reference to FIGS. 14 to 16. As to steps S1 to S22 shown in FIGS. 14 to 16, operations similarly to those at the step S1 to step S22 shown in FIG. 8 respectively are performed, and therefore the description thereof will not be made in the following.

Figure 14:
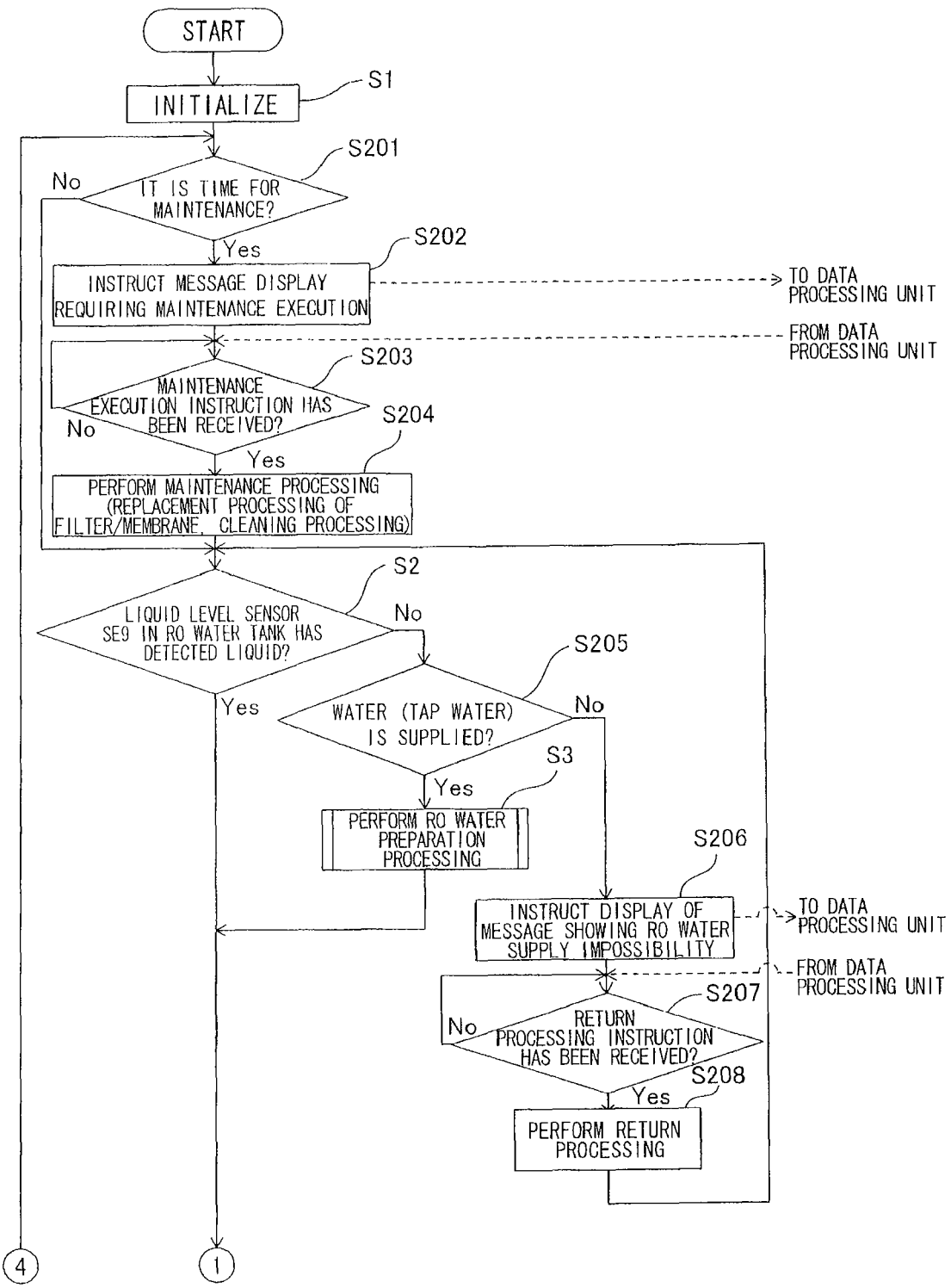
FIG. 14 is a flow chart for illustrating a reagent preparation processing operation of a blood analysis device according to the second embodiment of the present invention.

In the second embodiment, after the step S1 in FIG. 14, the CPU 47a determines whether or not it is time for maintenance of the reagent preparation device 104 at a step S201. For example, a filter 46c of an RO water preparation unit 46 is set to be replaced once every six months, an RO membrane 46b is set to be replaced once every one to two years, and cleaning of the RO water preparation unit 46 is set to be performed once every twelve weeks. If it is not the time for maintenance, the process advances to the step S2. On the other hand, if it is the time for maintenance, message display instruction information requiring maintenance execution is transmitted to the data processing unit 3 through a communication interface 47d at a step S202.

A data processing operation performed in the data processing unit 3 in transmission of the message display instruction information from the reagent preparation device 104 will be now described with reference to FIG. 17.

Figure 17:
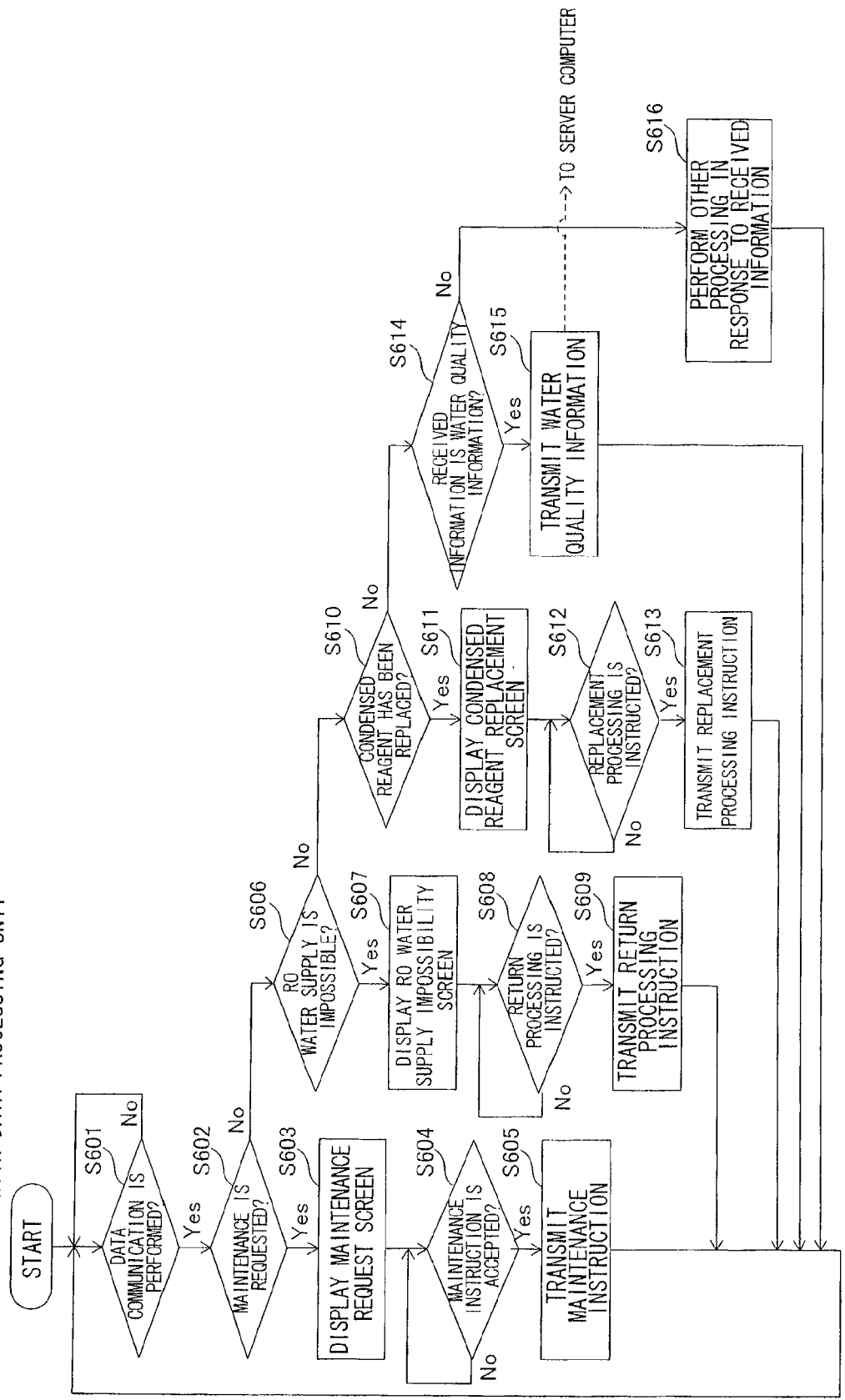
FIG. 17 is a flow chart for illustrating a data processing operation of a data processing unit of the blood analysis device according to the second embodiment of the present invention.

At a step S601 in FIG. 17, the CPU 31a determines whether or not data communication has been performed. More specifically, it is determined whether or not the message display instruction information such as maintenance execution request transmitted from the reagent preparation device 104 has been received through the communication interface 31i. This determination is repeated until the message display instruction information is received.

Figure 18:
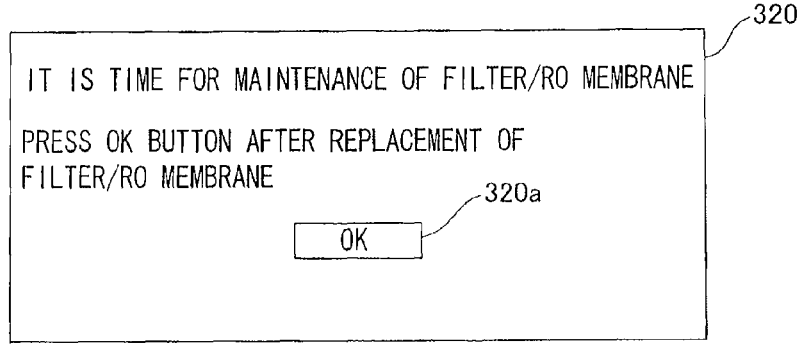
FIG. 18 is a diagram showing a maintenance request screen of the blood analysis device according to the second embodiment of the present invention.

It is determined that the received information is based on the maintenance execution request at a step S602, and the maintenance request screen is displayed on the display unit 32 at a step S603. More specifically, if the contents of the maintenance are replacement of the filter 46c and the RO membrane 46b, a maintenance request screen 320 of the filter 46c and the RO membrane 46b is displayed on the display unit 32, as shown in FIG. 18. A message stating that "it is time for maintenance of the filter/RO membrane" showing necessity of the maintenance of the filter 46c and the RO membrane 46b is displayed on the maintenance request screen 320. A message stating that "please press an OK bottom after replacement of the filter/RO membrane" facilitating the replacement of the filter 46c and the RO membrane 46b is also displayed on the maintenance request screen 320. An OK button 320a for accepting a maintenance processing instruction is further displayed on the maintenance request screen 320.

At a step S604, it is determined whether or not the maintenance processing instruction has been accepted on the basis of a state of press of the OK button 320a, and this determination is repeated until the OK button 320a is pressed. When the maintenance processing instruction is accepted, the maintenance processing instruction information is transmitted to the reagent preparation device 104 at a step S605.

In the reagent preparation device 104, after transmitting the message display instruction information of the maintenance execution request has been transmitted to the data processing unit 3 at the step S202 in FIG. 14, the CPU 47a determines whether or not the maintenance processing instruction information transmitted from the data processing unit 3 has been received at a step S203. This determination is repeated until the maintenance processing instruction information is received, and when received, maintenance processing is performed at a step S204. More specifically, the replacement processing of the filter 46c and the RO membrane 46b, the cleaning processing of the RO water preparation unit 46 or the like is performed in response to the contents of the maintenance If determining that the prescribed amount of RO water is not stored in the RO water tank 46a at the step S2, the CPU 47a determines whether or not the tap water is supplied to the RO water preparation unit 46 at a step S205. If it is supplied, RO water preparation processing is performed at the step S3.

An RO water preparation processing operation at the step S3 of the reagent preparation processing operation shown in FIG. 14 will be now described with reference to FIG. 19. As to steps S301 to S304 shown in FIG. 19, operations similar to those at the steps S301 to S304 shown in FIG. 9 are performed, and therefore the description thereof will not made in the following.

Figure 19:
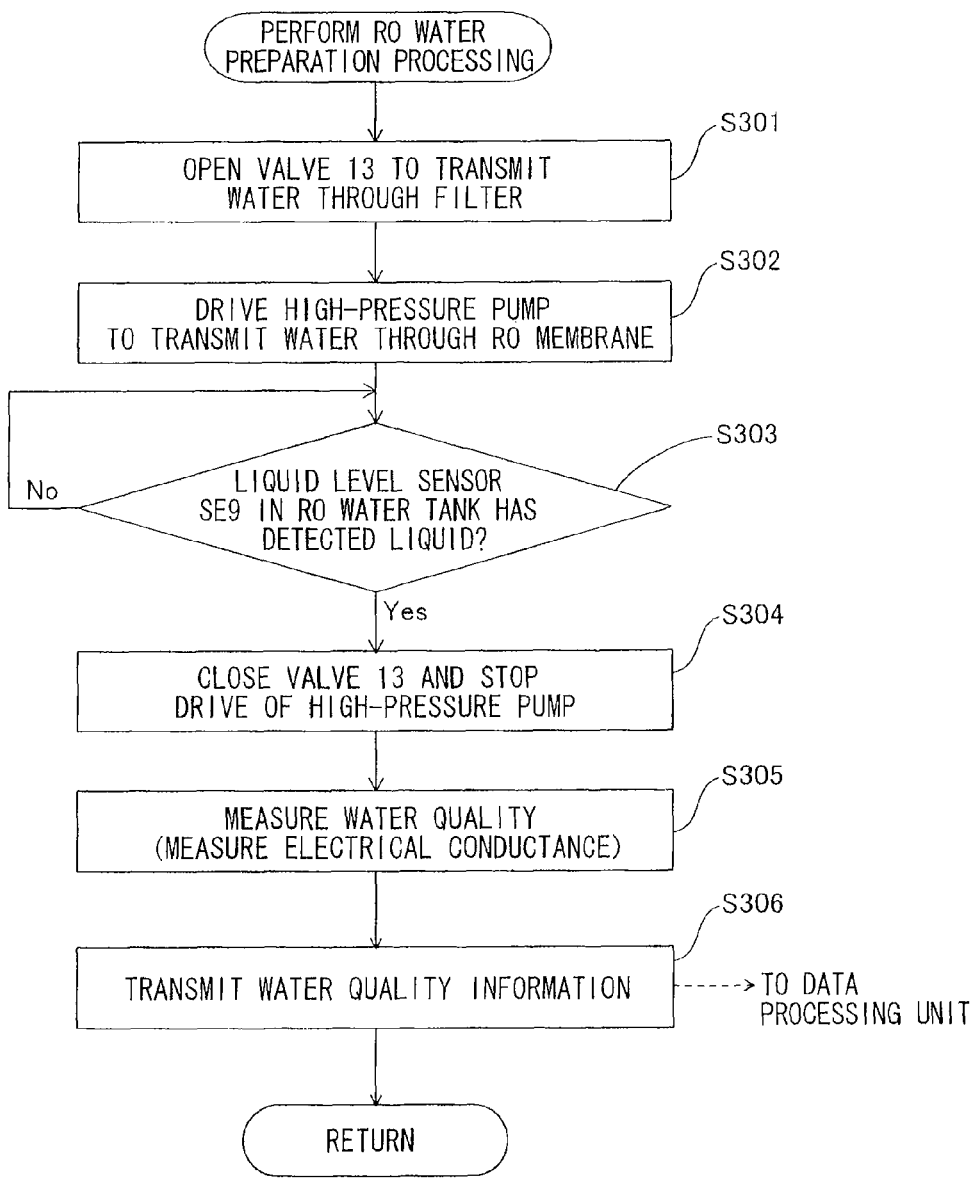
FIG. 19 is a flow chart for illustrating an RO water preparation processing operation at a step S3 of the reagent preparation processing operation shown in FIG. 14.

After stopping the drive of the high-pressure pump 46d at the step S304 in FIG. 19 in a state where the prescribed amount of RO water is stored in the RO water tank 46a, the conductivity sensor SE10 measures the electrical conductance of the RO water in the tank at a step S305. At a step S306, a measurement result of the electrical conductance as water quality information is transmitted to the data processing unit 3 through the communication interface 47d, and the RO water preparation processing operation ends.

When the water quality information is transmitted from the reagent preparation device 104, in the data processing unit 3, it is determined that the received information is water quality information at a step S614 after determination of steps S601, S602, S606 and S610 shown in FIG. 17. At a step S615, the received water quality information is transmitted to the server computer 300 through the network 200. The transmitted water quality information is stored in the server computer 300, and thereafter employed as information for determining the contents of a failure caused in the RO water preparation unit 46. A plurality of the water quality information obtained from a plurality of the blood analysis devices 100 connected through the network 200 is stored in the server computer 300, and the contents of a failure of the RO water preparation unit 46 can be determined with these plurality of water quality information. If the received information in the data processing unit 3 is not any of information based on the maintenance execution request, the RO water supply impossibility, the high-concentration reagent replacement and the water quality information, other processing in response to the received information, such as message display showing other failure caused in the reagent preparation device 104 is performed at a step S616.

On the other hand, if it is determined that the tap water is not supplied at the step S205 in FIG. 14, display instruction information of a message showing RO water supply impossibility is transmitted to the data processing unit 3 through the communication interface 47*d* at a step S206.

Figure 20:
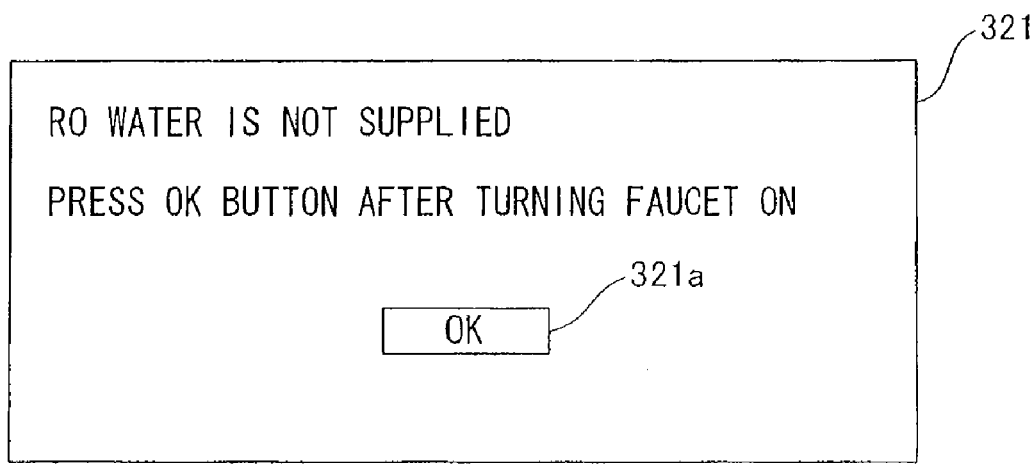
FIG. 20 is a diagram showing an RO water supply disapproval screen of the blood analysis device according to the second embodiment of the present invention.

When the display instruction information of the message showing the RO water supply impossibility is transmitted from the reagent preparation device 104, in the data processing unit 3, it is determined that the received information is based on the RO water supply impossibility at a step S606 after determination of the steps S601 and S602 shown in FIG. 17. At a step S607, an RO water supply impossible screen 321 is displayed on the display unit 32, as shown in FIG. 20. A message stating that "RO water is not supplied" showing an RO water supply impossible state is displayed on the RO water supply impossible screen 321. A message stating that "please press an OK bottom after turning a faucet on" facilitating supply of the tap water in order to solve this state is also displayed on the RO water supply impossible screen 321. An OK button 321*a* for accepting a return processing instruction of the RO water preparation processing operation is further displayed on the maintenance request screen 320.

At a step S608, it is determined whether or not the return processing instruction has been accepted on the basis of a state of press of the OK button 321*a*, and this determination is repeated until the OK button 321*a* is pressed. When the return processing instruction is accepted, the return processing instruction information is transmitted to the reagent preparation device 104 at a step S609.

In the reagent preparation device 104, after transmitting the display instruction information of the message showing the RO water supply impossibility has been transmitted to the data processing unit 3 at the step S206 in FIG. 14, it is determined whether or not the return processing instruction information transmitted from the data processing unit 3 has been received at a step S207. This determination is repeated until the return processing instruction information is received. If it is received, the return processing of the RO water preparation processing operation is performed at a step S208. More specifically, all of the RO water stored in the RO water tank 46*a* is discharged by opening the electromagnetic valve V15. Thus, old RO water left in the tank for a long period of time can be discharged without performing the RO water preparation processing operation, and hence the old RO water having a possibility of deterioration of water quality can be prevented from being employed in reagent preparation. Then, the operation advances to step S2 after performing the return processing.

Figure 15:
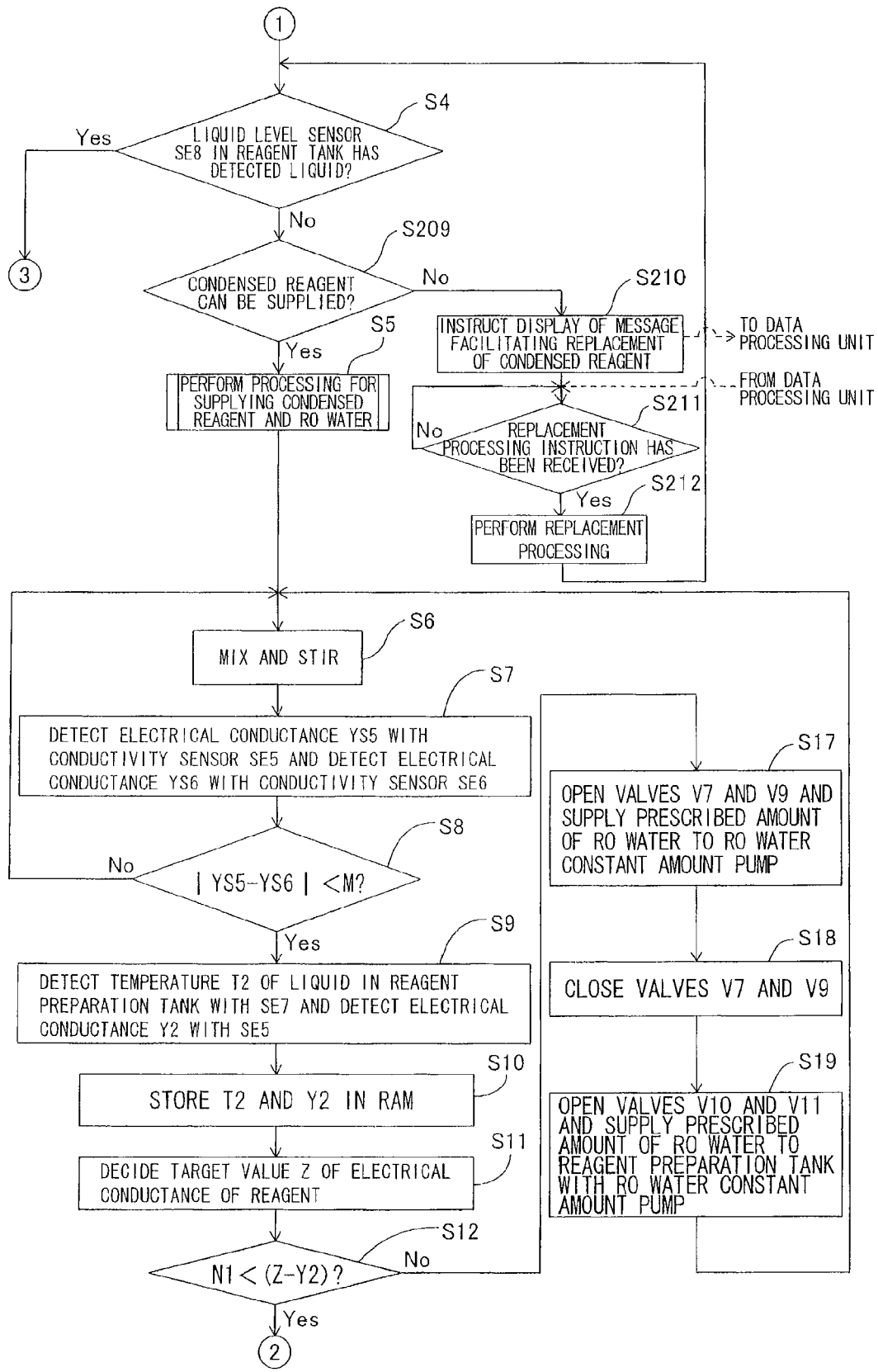
FIG. 15 is a flow chart for illustrating a reagent preparation processing operation of a blood analysis device according to the second embodiment of the present invention.
Figure 16:
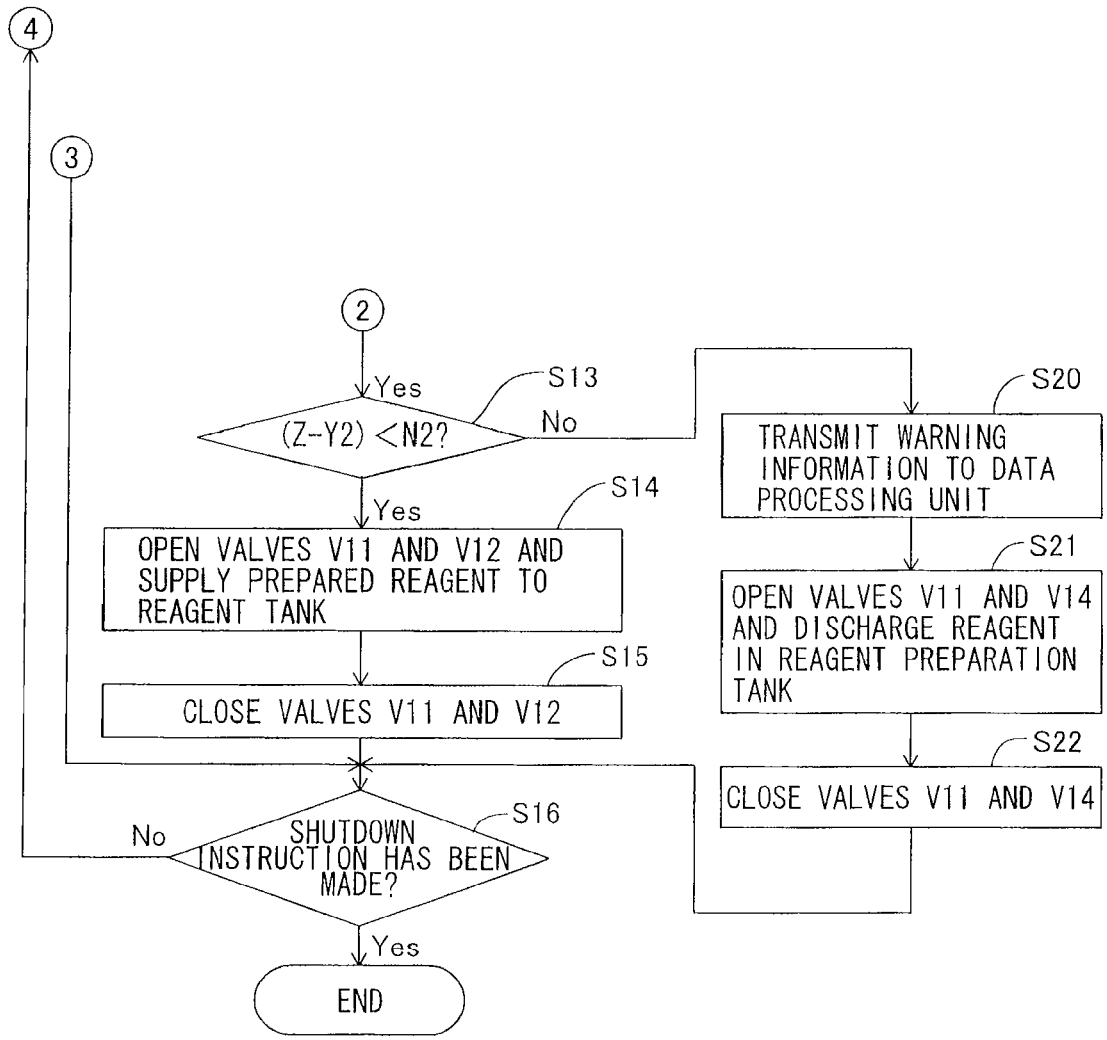
FIG. 16 is a flow chart for illustrating a reagent preparation processing operation of a blood analysis device according to the second embodiment of the present invention.

At the step S4 shown in FIG. 15, if it is determined that the prescribed amount of reagent is not stored in the reagent tank 45, it is determined whether or not the high-concentration reagent can be supplied from the high-concentration reagent tank 5 to the reagent constant amount tank 41 at a step S209. If it can be supplied, an supply processing operation of the high-concentration reagent and the RO water is performed at the step S5. On the other hand, if it cannot be supplied, the display instruction information of the message facilitating replacement of the high-concentration reagent tank 5 is transmitted to the data processing unit 3 through the communication interface 47*d* at a step S210.

Figure 21:
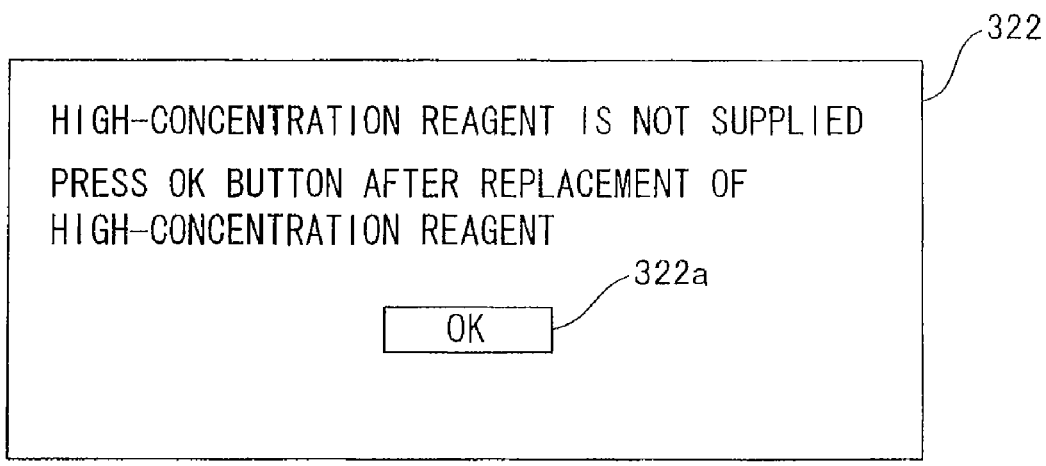
FIG. 21 is a diagram showing a high-concentration reagent exchange screen of the blood analysis device according to the second embodiment of the present invention.

When the display instruction information of the message facilitating the replacement of the high-concentration reagent tank 5 is transmitted from the reagent preparation device 104, in the data processing unit 3, it is determined that the received information is information for facilitating the replacement of the high-concentration reagent tank 5 at a step S610 after determination of the steps S601, S602 and S606 shown in FIG. 17. At a step S611, a high-concentration reagent replacement screen 322 is displayed on the display unit 32, as shown in FIG. 21. A message stating that "high-concentration reagent is not supplied" showing a high-concentration reagent supply impossible state is displayed on the high-concentration reagent replacement screen 322. A message stating that "please press an OK bottom after replacement of the high-concentration reagent" facilitating replacement of the high-concentration reagent tank 5 in order to solve this state is also displayed on the high-concentration reagent replacement screen 322. An OK button 322*a* for accepting an instruction of tank replacement processing for performing reagent preparation with the replaced high-concentration reagent is further displayed on the high-concentration reagent replacement screen 322.

At a step S612, it is determined whether or not the replacement processing instruction has been accepted on the basis of a state of press of the OK button 322*a*, and this determination is repeated until the OK button 322*a* is pressed. When the replacement processing instruction is accepted, the return processing instruction information is transmitted to the reagent preparation device 104 at a step S613.

In the reagent preparation device 104, after transmitting the display instruction information of the message facilitating the replacement of the high-concentration reagent tank 5 to the data processing unit 3 at the step S210 in FIG. 15, it is determined whether or not the replacement processing instruction information transmitted from the data processing unit 3 has been received at a step S211. This determination is repeated until the replacement processing instruction information is received. When it is received, the replacement processing of the high-concentration reagent tank 5 is performed at a step S212. More specifically, the electromagnetic valves V1 and V2 are opened, and the high-concentration reagent is supplied from the high-concentration reagent tank 5 to the reagent constant amount tank 41. Then, the operation advances to the step S4.

The remaining structure of the blood analysis device 100 according to the second embodiment is similar to that of the blood analysis device 1 of the aforementioned first embodiment.

According to the second embodiment, as hereinabove described, the reagent preparation device 104 is provided with the CPU 47*a* detecting the state of the reagent preparation device 104 and the state of the reagent preparation and the communication interface 47*d* for transmitting the state information detected by the CPU 47*a* to the data processing unit 3 provided outside the reagent preparation device 104, and the data processing unit 3 is so formed as to receive the state information transmitted from the reagent preparation device 104 and display the received state information on the display unit 32, whereby the state of the reagent preparation device 104, the state of the reagent preparation or the like can be confirmed by the display unit 32 of the data processing unit 3, and hence the situation of the reagent preparation device 104 can be easily visually recognized.

According to the second embodiment, the data processing unit 3 is so formed as to display the information for solving the state of the reagent preparation (the RO water supply impossible state and the high-concentration reagent supply impossible state) in the reagent preparation device 104 on the display unit 32, whereby the user can be easily recognized a method for solving the failure of the reagent preparation on the basis of the information displayed on the display unit 32, and hence the failure can be easily handled.

According to the second embodiment, the OK buttons 320*a*, 321*a* and 322*a* accepting the operation instructions (the maintenance processing instruction, the return processing instruction and the replacement processing instruction) for the reagent preparation device 104 are displayed on the display unit 32, and the data processing unit 3 is so formed that the operation instruction information based on the received operation instruction is transmitted to the reagent preparation device 104, and the reagent preparation device 104 is so formed as to perform the operations (the maintenance processing, the return processing and the replacement processing) according to the received operation instruction information, whereby the user can easily perform a prescribed operation instruction for the reagent preparation device 104 by an easy operation from the display unit 32.

The remaining effects of the second embodiment are similar to those of the aforementioned first embodiment.

The embodiment disclosed this time must be considered as illustrative in all points and not restrictive. The range of the present invention is shown not by the above description of the embodiment but by the scope of claim for patent, and all modifications within the meaning and range equivalent to the scope of claim for patent are included.

For example, while the CPU 47a determines whether or not the difference (Z−Y2) between the target value Z of the electrical conductance and the detection value Y2 is larger than the prescribed value N1 at the step S12 of the reagent preparation processing operation shown in FIG. 8, and if the difference (Z−Y2) is smaller than the prescribed value N1, the RO water is additionally supplied to the reagent preparation tank 43 by the RO water constant amount pump 44 at the steps S17 to 19 in the aforementioned first embodiment, the present invention is not restricted to this. A reagent preparation processing operation of a blood analysis device according to another embodiment of the present invention will be hereinafter described.

Figure 11:
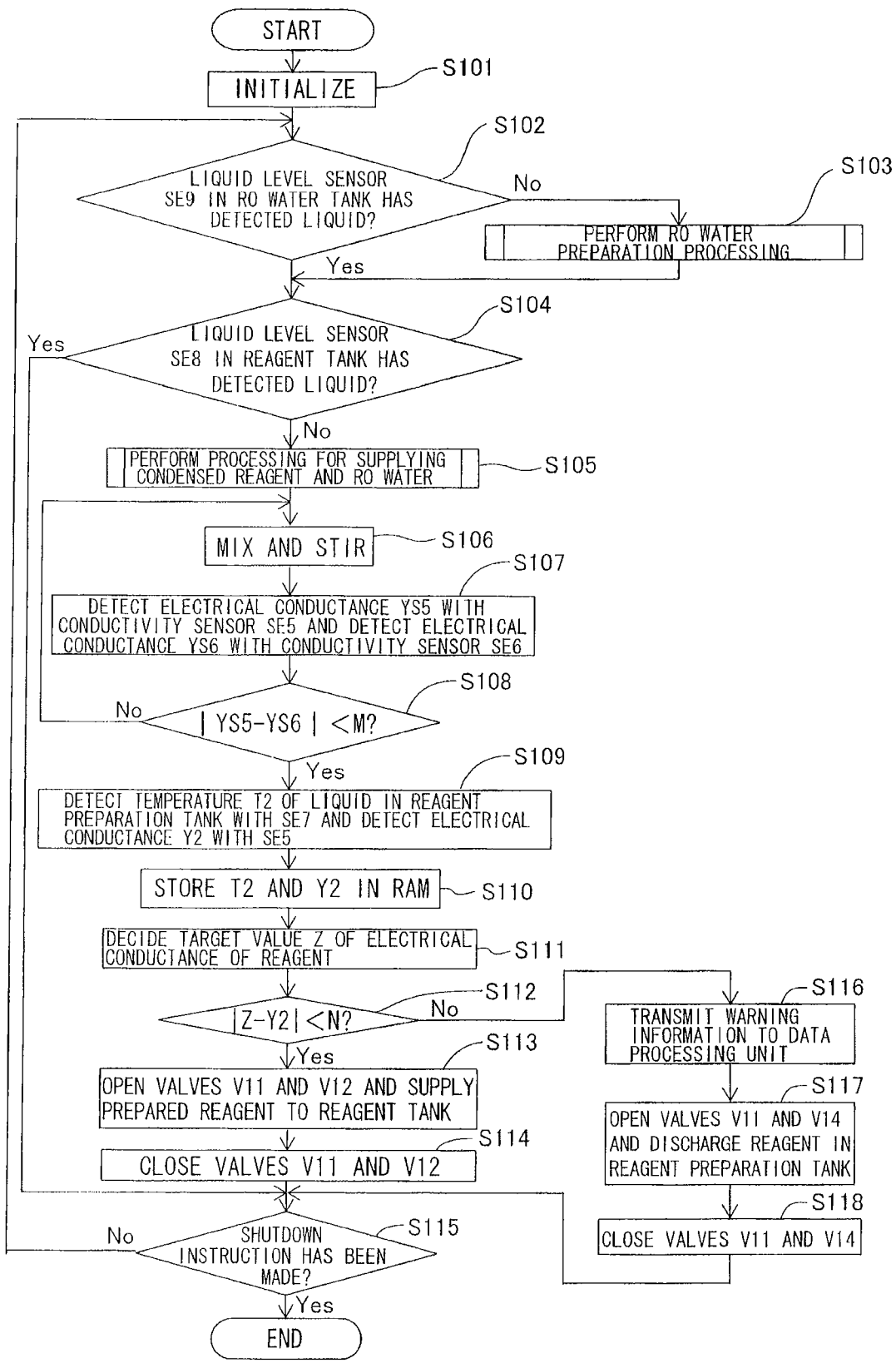
FIG. 11 is a flow chart for illustrating a reagent preparation processing operation of a blood analysis device according to another embodiment of the present invention.

In the reagent preparation processing operation shown in FIG. 11, processing similar to the processing at the steps S1 to 11 shown in FIG. 8 is performed at steps S101 to 111 by a CPU 47a.

At a step S112, the CPU 47a determines whether or not an absolute value |Z−Y2| between a target value Z and a detection value Y2 is smaller than a prescribed value N. If the absolute value |Z−Y2| is larger than the prescribed value N, a reagent in a reagent preparation tank 43 has not been diluted at a desired concentration, and hence the CPU 47a transmits warning information showing that the reagent with the desired concentration has not been prepared to a data processing unit 3 through a communication interface 47d at a step S116. When a CPU 31a of the data processing unit 3 receives the aforementioned warning information through a communication interface 31i, a message stating that the reagent with the desired concentration has not been prepared in a reagent preparation device 4 is displayed on a display unit 32. Thus, the user can easily know that the reagent has not been prepared at the desired concentration. At a step S117, electromagnetic valves V11 and V14 are opened by the CPU 47a of the reagent preparation device 4, and the reagent in the reagent preparation tank 43 is discharged outside the reagent preparation device 4. Then, the CPU 47a closes the electromagnetic valves V11 and V14 at a step S118 after discharging the reagent in the reagent preparation tank 43 outside the reagent preparation device 4.

If the absolute value |Z−Y2| is smaller than the prescribed value N, the reagent in the reagent preparation tank 43 is prepared at the desired concentration, and hence processing similar to the processing at the steps S14 to S16 shown in FIG. 8 is performed at steps S113 to S115 by the CPU 47a. The reagent preparation processing operation according to another embodiment of the present invention is performed in the aforementioned manner.

While each of the aforementioned first and second embodiments has shown the example of applying the present invention to the blood analysis device which is an exemplary sample treating device and sample analysis system, the present invention is not restricted to this but is also applicable to an immunoanalyzer or a biochemical analyzer. Alternatively, other sample treating device and sample analysis system such as a smear preparation device may be applicable so far as it is a sample treating device and a sample analysis system each performing sample processing with a reagent.

While the aforementioned first embodiment has shown the example in which the detection value of the electrical conductance approaches the target value in order to dilute the high-concentration reagent at the desired concentration, the present invention is not restricted to this but the high-concentration reagent may be diluted at the desired concentration with electric resistivity ($\rho=1/\alpha$) which is an inverse of the electrical conductance ($\alpha$).

While the aforementioned first embodiment has shown the example in which the target value of the electrical conductance of the reagent obtained by mixing and stirring the high-concentration reagent and the RO water is decided according to the aforementioned formula (2), the present invention is not restricted to this but the target value may be decided with a table in which the electrical conductance of the RO water and the target value of the electrical conductance of the liquid obtained by mixing and stirring the high-concentration reagent and the RO water are correspond to each other, for example.

While the aforementioned first embodiment has shown the example of providing the two conductivity sensors in the reagent preparation tank, the present invention is not restricted to this but one conductivity sensor may be provided, or three or more conductivity sensor may be provided.

While the conductivity sensor SE3 detecting the electrical conductance of the RO water is provided in the RO water constant amount tank 42 and the conductivity sensor SE5 detecting the electrical conductance of the liquid obtained by mixing and stirring the high-concentration reagent and the RO water is provided in the reagent preparation tank 43 in the aforementioned first embodiment, the present invention is not restricted to this but the reagent preparation device 4 may be so formed as to supply the high-concentration reagent into the reagent preparation tank 43 after supplying the RO water into the reagent preparation tank 43, and the conductivity sensor provided in the reagent preparation tank 43 may detect the electrical conductance of the RO water, and then the electrical conductance of the liquid obtained by mixing and stirring the high-concentration reagent and the RO water may be detected. According to this structure, the electrical conductance of the RO water and the electrical conductance of the liquid obtained by mixing and stirring the high-concentration reagent and the RO water can be detected simply by providing the one conductivity sensor in the reagent preparation tank 43. Thus, the structure of the reagent preparation device 4 can be simplified.

While the reagent in the reagent preparation tank 43 is discharged outside the reagent preparation device 4 when the concentration of the reagent in the reagent preparation tank 43 is lower than the desired concentration in the aforementioned first embodiment, the present invention is not restricted to this but a high-concentration reagent constant amount pump capable of additionally gradually supplying the high-concentration reagent to the reagent preparation tank may be provided, and the high-concentration reagent may be additionally gradually supplied to the reagent preparation tank by the high-concentration reagent constant amount pump when the concentration of the reagent in the reagent preparation tank 43 is lower than the desired concentration. Thus, the reagent with the desired concentration can be prepared without wasting the reagent in the reagent preparation tank 43.

While the warning information showing that the reagent has not been prepared at the desired concentration is transmitted from the CPU 47a of the reagent preparation device 4 to the data processing unit 3 and the CPU 31a of the data processing unit 3 displays the message stating that the reagent with the desired concentration has not been prepared on the display unit 32, when the reagent in the reagent preparation tank 43 has not been prepared at the desired concentration in the aforementioned first embodiment, the present invention is not restricted to this but an alarm showing that the reagent has not been prepared at the desired concentration may be emitted from the reagent preparation device 4. Alternatively, the reagent preparation device 4 may comprises a display, and a message stating that the reagent with the desired concentration has not been prepared may be displayed on the display of the reagent preparation device 4. The user can easily know that the reagent has not been prepared at the desired concentration also by this.

While the control unit 47 provided in the reagent preparation device 4 performs the decision processing deciding the target value of the electrical conductance of the liquid obtained by mixing and stirring the high-concentration reagent and the dilution liquid and the determination processing determining whether or not the electrical conductance detected by the conductivity sensor SE5 is in the prescribed range with respect to the target value in the aforementioned first embodiment, the present invention is not restricted to this but the control unit 31 provided in the data processing unit 3 may perform the aforementioned decision and determination processing.

While each of the aforementioned first and second embodiments has shown the example of providing the data processing unit separately from the measurement unit, the present invention is not restricted to this but the data processing unit may be incorporated in the measurement unit.

While each of the aforementioned first and second embodiments has shown the example of providing the reagent preparation device separately from the measurement unit, the present invention is not restricted to this but the reagent preparation device may be incorporated in the measurement unit.

While the blood analysis device constituted by the measurement unit, the data processing unit and the reagent preparation device has shown as an exemplary sample analysis system in the aforementioned second embodiment, the present invention is not restricted to this but it may be a blood analysis device constituted by the measurement unit and the reagent preparation device, not including the data processing unit. In this case, the reagent preparation device may simply be formed to allow communication of the state information of the reagent preparation device with the computer provided outside and the external computer may simply be formed to display the state information on the display of the computer.

While the aforementioned second embodiment has shown the example of displaying the message showing the high-concentration reagent supply impossible state, the message facilitating the replacement of the high-concentration reagent and the OK button as the preparation instruction acceptance screen on the common high-concentration reagent replacement screen, the present invention is not restricted to this but the message showing the high-concentration reagent supply impossible state, the message facilitating the replacement of the high-concentration reagent, the OK button as the preparation instruction acceptance screen may be displayed on respective separate display screens.

While the aforementioned second embodiment has shown the example of displaying the message showing the necessity of the maintenance, the message facilitating execution of the maintenance and the OK button as the maintenance instruction acceptance screen on the common maintenance request screen, the present invention is not restricted to this but the message showing the necessity of the maintenance, the message facilitating execution of the maintenance and the OK button as the maintenance instruction acceptance screen may be displayed on respective separate display screens.

What is claimed is:

1. A sample analysis system comprising:
    a reagent preparation unit for preparing a reagent employed in sample measurement by diluting a high-concentration reagent with a dilution liquid; and
    a measurement unit connected to said reagent preparation unit and for measuring a sample with said reagent prepared by said reagent preparation unit, wherein
    said reagent preparation unit comprises a state detector for detecting at least one of a state of said reagent preparation unit and a state of reagent preparation by said reagent preparation unit, and a transmission unit for transmitting state information detected by said state detector to a computer arranged outside said reagent preparation unit,
    said computer comprises a display, receives said state information transmitted by said transmission unit of said reagent preparation unit, and displays received said state information on said display.

2. The sample analysis system according to claim 1, further comprising a data processing unit constituted by said computer, for displaying a measurement result by said measurement unit on said display, receiving said state information transmitted by said transmission unit of said reagent preparation unit, and displaying received said state information on said display.

3. The sample analysis system according to claim 2, wherein
    said sample analysis system is connected to a server computer, and
    said data processing unit transmits received said state information to said server computer.

4. The sample analysis system according to claim 3, wherein
    said reagent preparation unit further comprises a dilution liquid purification unit for purifying said dilution liquid from tap water, and
    said state detector of said reagent preparation unit detects a state of the dilution liquid purified by said dilution liquid purification unit,
    said transmission unit of said reagent preparation unit transmits state information of detected said dilution liquid to said data processing unit, and
    said data processing unit transmits state information of received said dilution liquid to said server computer.

5. The sample analysis system according to claim 1, wherein
    said computer is configured to display state resolving information showing information for resolving said state shown by received said state information on said display together with received said state information.

6. The sample analysis system according to claim 1, wherein
    said computer displays an instruction receiving screen for receiving an operation instruction to said reagent preparation unit on said display, and transmits operation instruction information based on received said operation instruction to said reagent preparation unit when said operation instruction is received by said instruction receiving screen, and said reagent preparation unit receives said operation instruction information transmitted by said computer, and controls an operation of said reagent preparation unit in accordance with received said operation instruction information.

7. The sample analysis system according to claim 6, wherein said state detector of said reagent preparation unit detects a high-concentration reagent supply impossible state in which said high-concentration reagent is not supplied to said reagent preparation unit, said transmission unit of said reagent preparation unit transmits information showing said high-concentration reagent supply impossible state to said computer, said computer displays a message showing said high-concentration reagent supply impossible state, a message facilitating replacement of said high-concentration reagent, and a preparation instruction receiving screen for receiving an instruction of preparation of said reagent which is performed with a replaced high-concentration reagent, and transmits preparation instruction information based on received said preparation instruction to said reagent preparation unit when said preparation instruction is received by said preparation instruction receiving screen, and said reagent preparation unit receives said preparation instruction information transmitted by said computer, and executes said preparation of said reagent which is performed with said replaced high-concentration reagent.

8. The sample analysis system according to claim 6, wherein said state detector of said reagent preparation unit detects a maintenance required state which is a state where maintenance of a prescribed unit of said reagent preparation unit is required, said transmission unit of said reagent preparation unit transmits information showing said maintenance required state to said computer, said computer displays a message showing said maintenance required state, a message facilitating execution of said maintenance, and a maintenance instruction receiving screen receiving an execution instruction of said maintenance, and transmits maintenance instruction information based on received said execution instruction of said maintenance to said reagent preparation unit when said execution instruction of said maintenance is received by said maintenance instruction receiving screen, and said reagent preparation unit receives said maintenance instruction information transmitted by said computer, and executes said maintenance which said computer has received.

9. The sample analysis system according to claim 8, wherein said reagent preparation unit further comprises a dilution liquid purification unit for purifying said dilution liquid from tap water, and said maintenance comprises a cleaning operation of said dilution liquid purification unit.

10. The sample analysis system of claim 1, wherein:
the sample is a blood; and
the measurement unit is configured to dilute the blood with the reagent prepared by the reagent preparation unit, and is configured to measure a blood cell included in the diluted blood.

11. A reagent preparation device, constituted to prepare a reagent employed in sample measurement by diluting a high-concentration reagent with a dilution liquid, comprising:

a reagent preparation unit for preparing the reagent;

a state detector for detecting at least one of a state of the reagent preparation unit and a state of reagent preparation by the reagent preparation unit; and a transmission unit for transmitting state information detected by said state detector to a computer arranged outside said reagent preparation device, wherein said computer comprises a display, receives said state information transmitted by said transmission unit, and displays received said state information on said display, said computer further displays an instruction receiving screen for receiving an operation instruction to said reagent preparation unit on said display, and transmits operation instruction information based on receiving said operation instruction to said reagent preparation unit when said operation instruction is received by said instruction receiving screen, and said reagent preparation unit receives said operation instruction information transmitted by said computer, and controls an operation of said reagent preparation unit in accordance with receiving said operation instruction information.

12. A reagent preparation device for preparing a reagent employed in sample processing device by diluting a high-concentration reagent with a dilution liquid, comprising:

a storage unit storing said high-concentration reagent and said dilution liquid;

first supplier for supplying said dilution liquid to said storage unit;

a detector for detecting a value regarding a prescribed feature of said dilution liquid;

second supplier for supplying said high-concentration reagent to said storage unit;

a controller for controlling said first supplier to supply a prescribed amount of said dilution liquid to said storage unit, for controlling said second supplier to supply a prescribed amount of said high-concentration reagent to said storage unit, and for deciding a target value of a value regarding said prescribed feature of a liquid obtained by mixing said high-concentration reagent and said dilution liquid in said storage unit, on the basis of a detection value detected by said detector.

13. The reagent preparation device according to claim 12, further comprising:

a second detector for detecting a value regarding said prescribed feature of the liquid obtained by mixing said high-concentration reagent and said dilution liquid, wherein said controller determines whether or not a second detection value detected by said second detector is in a prescribed range with respect to said target value.

14. The reagent preparation device according to claim 13, wherein said detector is configured to detect electrical conductance of said dilution liquid as a value regarding said prescribed feature, and said second detector is configured to detect electrical conductance of the liquid obtained by mixing said high-concentration reagent and said dilution liquid as a value regarding said prescribed feature.

15. The reagent preparation device according to claim 14, further comprising:
- a first temperature measurement unit measuring a temperature of said dilution liquid; and
- a second temperature measurement unit measuring a temperature of the liquid obtained by mixing said high-concentration reagent and said dilution liquid, wherein
- said controllers decides a target value of electrical conductance of said liquid obtained by mixing said high-concentration reagent and said dilution liquid on the basis of a mixing ratio of said high-concentration reagent and said dilution liquid in a case where said high-concentration reagent is diluted at a desired concentration, electrical conductance detected by said detector, a measurement value measured by said first temperature measurement unit, a measurement value measured by said second temperature measurement unit and electrical conductance of said high-concentration reagent.

16. The reagent preparation device according to claim 13, further comprising warning information output unit for outputting warning information showing that said high-concentration reagent has not been diluted at a desired concentration to a user when said second detection value is not in said prescribed range with respect to said target value.

17. The reagent preparation device according to claim 13, wherein
- said controller controls said first supplier or said second supplier to additionally supply said dilution liquid or said high-concentration reagent to said storage unit when said second detection value is not in said prescribed range with respect to said target value.

18. The reagent preparation device according to claim 17, wherein
- said first supplier comprises constant amount supplier for supplying said prescribed amount of said dilution liquid to said storage unit and additional supplier for additionally supplying said dilution liquid to said storage unit.

19. The reagent preparation device according to claim 13, further comprising:
- a stirring unit stirring said high-concentration reagent and said dilution liquid in said storage unit; and
- a third detection unit detecting a value regarding said prescribed feature of a liquid obtained by stirring said high-concentration reagent and said dilution liquid by said stirring unit, wherein
- said second detector and said third detector are provided on respective different positions in said storage unit, and
- said controller controls said stirring unit to stir the liquid in said storage unit such that said second detection value and a third detection value detected by said third detection unit are substantially the same.

20. The reagent preparation device according to claim 12, further comprising a dilution liquid preparation unit for preparing said dilution liquid.

21. The reagent preparation device according to claim 20, wherein
- said dilution liquid preparation unit is configured to prepare RO water using a reverse osmosis membrane.

22. The reagent preparation device according to claim 12, wherein
- said detection unit is configured to detect a value regarding said prescribed feature of the liquid obtained by mixing said high-concentration reagent and said dilution liquid; and
- said controller determines whether or not a value regarding said prescribed feature of the liquid obtained by mixing said high-concentration reagent and said dilution liquid, detected by said detection unit is in a prescribed range with respect to said target value.

* * * * *